US010293056B1

(12) United States Patent
Ramesh et al.

(10) Patent No.: US 10,293,056 B1
(45) Date of Patent: May 21, 2019

(54) METHODS AND COMPOSITIONS FOR NON-VIRAL GENE THERAPY FOR TREATMENT OF HYPERPROLIFERATIVE DISEASES

(75) Inventors: Rajagopal Ramesh, Houston, TX (US); Jack A. Roth, Houston, TX (US); Tomoyuki Saeki, Tokyo (JP); Deborah R. Wilson, Houston, TX (US)

(73) Assignees: Board of Regents, The University of Texas System, Austin, TX (US); Introgen Research Institute, Inc., Austin, TX (US)

(*) Notice: Subject to any disclaimer, the term of this patent is extended or adjusted under 35 U.S.C. 154(b) by 1792 days.

(21) Appl. No.: 09/575,473

(22) Filed: May 24, 2000

(51) Int. Cl.
*A61K 48/00* (2006.01)

(52) U.S. Cl.
CPC .................................. *A61K 48/00* (2013.01)

(58) Field of Classification Search
USPC ........................................... 424/450; 514/44
See application file for complete search history.

(56) References Cited

U.S. PATENT DOCUMENTS

| | | | |
|---|---|---|---|
| 5,399,363 A | 3/1995 | Liversidge et al. | 424/490 |
| 5,401,511 A | 3/1995 | Margalit | 424/450 |
| 5,432,260 A | 7/1995 | Stahl | 530/322 |
| 5,466,468 A | 11/1995 | Schneider et al. | 424/450 |
| 5,543,158 A | 8/1996 | Gref et al. | 424/501 |
| 5,603,872 A | 2/1997 | Margalit | 264/14.3 |
| 5,633,016 A | 5/1997 | Johnson | 424/649 |
| 5,641,515 A | 6/1997 | Ramtoola | 424/189 |
| 5,641,662 A * | 6/1997 | Debs et al. | |
| 5,656,016 A | 8/1997 | Ogden | 601/2 |
| 5,676,954 A | 10/1997 | Brigham | 424/450 |
| 5,677,144 A * | 10/1997 | Ullrich et al. | |
| 5,697,899 A | 12/1997 | Hillman et al. | 604/28 |
| 5,739,169 A | 4/1998 | Ocain et al. | 514/658 |
| 5,747,469 A * | 5/1998 | Roth et al. | 514/44 |
| 5,766,591 A * | 6/1998 | Brooks et al. | |
| 5,770,219 A | 6/1998 | Chiang et al. | 424/448 |
| 5,779,708 A | 7/1998 | Wu | 606/80 |
| 5,783,208 A | 7/1998 | Venkateshwaran et al. | 424/448 |
| 5,786,214 A | 7/1998 | Holmberg | 435/375 |
| 5,797,898 A | 8/1998 | Santini, Jr. et al. | 604/890.1 |
| 5,798,339 A | 8/1998 | Brandes | 514/34 |
| 5,801,005 A | 9/1998 | Cheever et al. | 435/7.24 |
| 5,811,128 A | 9/1998 | Tice et al. | 424/501 |
| 5,824,311 A | 10/1998 | Greene et al. | 424/138.1 |
| 5,824,346 A | 10/1998 | Dugan | 424/649 |
| 5,827,703 A | 10/1998 | Debs et al. | 435/172.3 |
| 5,830,880 A | 11/1998 | Sedlacek et al. | 514/44 |
| 5,846,225 A | 12/1998 | Rosengart et al. | 604/115 |
| 5,846,233 A | 12/1998 | Lilley et al. | 604/414 |
| 5,846,945 A | 12/1998 | McCormick | 514/44 |
| 5,849,718 A | 12/1998 | Grosveld | 514/44 |
| 5,851,829 A * | 12/1998 | Marasco et al. | |
| 5,871,727 A | 2/1999 | Curiel | 424/93.2 |
| 5,879,703 A | 3/1999 | Fountain | 424/450 |
| 5,889,155 A | 3/1999 | Ashkenazi et al. | 530/351 |
| 5,891,468 A * | 4/1999 | Martin et al. | 424/450 |
| 5,902,584 A | 5/1999 | Nicholson et al. | 424/143.1 |
| 5,919,643 A * | 7/1999 | Kelley et al. | |
| 5,928,884 A * | 7/1999 | Croce et al. | 435/7.23 |
| 5,962,265 A * | 10/1999 | Norris et al. | |
| 6,037,357 A * | 3/2000 | Hu | |
| 6,045,999 A * | 4/2000 | Bernards et al. | |
| 6,054,561 A * | 4/2000 | Ring | |
| 6,056,973 A * | 5/2000 | Allen et al. | |
| 6,071,533 A * | 6/2000 | Papahadjopoulos et al. | |
| 6,133,416 A * | 10/2000 | Wilson et al. | 530/300 |
| 6,165,737 A * | 12/2000 | Wang et al. | |

FOREIGN PATENT DOCUMENTS

| | | | |
|---|---|---|---|
| WO | WO 93/24640 | | 12/1993 |
| WO | WO 98/07408 | * | 2/1998 |
| WO | WO-98/07408 A1 | * | 2/1998 |
| WO | WO 98/20857 | | 5/1998 |
| WO | WO 99/18933 | | 4/1999 |

OTHER PUBLICATIONS

Ramesh et al (Mar. 2000) Proceedings of the American Association for Cancer Research Annual Meeting, No. 41, pp. 603.*
Verma et al (997) Nature, 389:239-242).*
Luo et al (2000) Nature Biotechnology, 18:33-37.*
Fox, (Feb. 2000) ASM News, vol. 66 (2): 1-3.*
Tilbrook et al (1997) EMBO J., 16: 1610-1619.*
Verma et al 1997) (Nature (1997) 389:239-242.*
Palù et al (1999) J. Biotechnol. 68:1-13.*
Gorecki (1999) Emerging Drugs 4:247-261.*
Hartwell et al., Integrating genetic approaches into discovery of anticaner drugs, 1997, Science, vol. 278, pp. 1064-1068.*
Crystal, Transfer of genes to humans: Early lessons and obstacles to success, 1995, Science, vol. 270, pp. 404-410.*
Gomez-Navarro et al., Gene therapy for cancer, 1999, European Journal of Cancer, vol. 35, pp. 867-885.*
Sigmund, Viewpoint: Are studies in genetically altered mice out of control, 2000, Arterioscler Thromb. Vasc. Biol., vol. 20, pp. 1425-1429.*
Jiang et al. The melanoma differentiation associated gene mda-7 suppresses cancer cell growth. Proc Natl Acad Sci U S A. Aug. 20, 1996;93(17):9160-5*

(Continued)

*Primary Examiner* — Catherine S Hibbert
(74) *Attorney, Agent, or Firm* — Parker Highlander PLLC

(57) ABSTRACT

The present invention relates to non-viral gene therapy methods and compositions for treatment of hyperproliferative disease in humans. More specifically, the invention is directed, in one embodiment, to lipid formulations which form stable liposome structures, capable of efficient in vivo nucleic acid transfer. In other embodiments, methods and compositions are directed to liposome transfer of anti-proliferative nucleic acids, wherein the transfer of the nucleic acids is cell specific via cell specific targeting moieties. The present invention, thus provides non-viral, liposome compositions and methods of gene transfer particularly useful for targeting and treating hyperproliferative disease.

38 Claims, 10 Drawing Sheets
Specification includes a Sequence Listing.

(56) References Cited

OTHER PUBLICATIONS

McCormick F. Cancer gene therapy: fringe or cutting edge? Nat Rev Cancer. Nov. 2001;1(2):130-41.*
The National Cancer Institute, Online at http://www.cancer.gov/cancerinfo/types.*
Buttgereit et al. Gene therapy of lymphoma. J Hematother Stem Cell Res. Jun. 2002;11(3):457-67.*
Greco, M. "Achievements and obstacles to progress in cancer surgery" in Oxford Textbook of Oncology, vol. 1, (Peckham, Pinedo and Umberto eds.), Oxford University Press, NY, 1995, pp. 865-867.*
Siprashvili et al. Replacement of Fhit in cancer cells suppresses tumorigenicity. Proc Nati Acad Sci U S A. Dec. 9, 1997;94(25):13771-6.*
Gura (1997) Science 278:1041-1042.*
Gromeier et al. (2001) Curr. Opin. Mol. Ther. 3:503-508.*
Dermer (1994) Bio/Technol. 12:320.*
Shafer et al. (2003) Int. J. Oncol. 23:389-400.*
Hsieh et al. (1999) Exp. Cell Res. 249:109-115.*
Janmaat et al. (2003) Clin. Cancer Res. 9:2316-2326.*
Wagener (Molecular Oncology: prospects for cancer diagnosis and therapy, published online at http://www.roche.com/pages/downloads/company/pdf/rtpenzberg01e.pdf, downloaded Mar. 12, 2008.*
Aksentijevich et al., "In vitro and in vivi liposome-mediated gene transfer leads to human MDR1 expression in mouse bone marrow progenitor cells," Human Gene Ther.7:1111, 1996.
Feigner et al.,"Lipofection: A highly efficient, lipid-mediated DNA-transfection procedure," Proc. Natl. Acad. Sci. USA 84:7413-7417, 1987.
Fraley et al., "Entrapment of a bacterial plasmid in phospholipid vesicles: Potential for gene transfer," Proc. Nat'l Acad. Sci. USA, 76:3348-3352, 1979.
Gabizon et al., "Effect of liposome composition and other factors on the targeting of liposomes to experimental tumors: biodistribution and imaging studies," Cancer Res., 50:6371-8, 1990.
Xu et al., "Parenteral gene therapy with p53 inhibits human breast tumors in vivo through an bystander mechanism without evidence of toxicity," Human Gene Therapy, 8:177-185, 1997.
Chen and Mixson, "Systemic gene therapy with p53 inhibits breast cancer: recent advances and therapeutic implications," Frontiers in Bioscience, 3:997-1004, 1998.
Ramesh et al., "Inhibition of primary and disseminated human lung cancers by systemic delivery of p53 tumor suppressor gene using an improved liposome," Proc. Am. Assoc. Cancer Res., 41:603, 2000 (Abstract No. 3841).
De Ruysscher et al., "Radical treatment of non-small-cell lung cancer patients with synchronous oligometastases: long-term results of a prospective phase II trial (Nct01282450)," J Thorac Oncol., 7:1547-1555, 2012.
Kvols, "Radiation sensitizers: a selective review of molecules targeting DNA and non-DNA targets," J Nucl Med, 46:187S-190S, 2005.
Rusthoven et al., "Multi-institutional phase I/II trial of stereotactic body radiation therapy for lung metastases," J Clin Oncol, 27(10):1579-1584, 2009.
Ghosh and Bachhawat, "Targeting of liposomes to hepatocytes," In: Liver diseases, targeted diagnosis and therapy using specific receptors and ligands, Wu G. and C. Wu ed. New York: Marcel Dekker, pp. 87-104, 1991.
Kaneda et al., "Increased expression of DNA cointroduced with nuclear protein in adult rat liver," Science, 243:375-378, 1989.
Kataoka et al., "An agent that increases tumor suppressor transgene product coupled with systemic transgene delivery inhibits growth of metastatic lung cancer in vivo," Cancer Res., 58: 4761-4765, 1998.
Kato et al., "Expression of hepatitis β virus surface antigen in adult rat liver," J. Biol Chem., 266:3361-3364, 1991.
Liu et al., "Cationic liposome-mediated intraveneous gene delivery," J. Biol. Chem., 270:24864, 1995.
Martin, in Specialized Drug Delivery Systems—Manufacturing and Production Technology, (P. Tylc Ed.) Marcel Dekker, New York, pp. 267-316, 1990.
Nicolau et al., "Liposomes as carriers for in vivo gene transfer and expression," Methods Enzymol., 149:157-176, 1987.
Nicolau and Sene, "Liposome-mediated DNA transfer in eukaryotic cells: Dependance of the transfer efficiency upon the type of liposomes used and the host cell cycle stage," Biochem. Biophys. Acta, 721:185-190, 1982.
Philip et al., "In vivo gene delivery: Efficient transfection of T lymphocytes in adult mice," J. Biol. Chem., 268:16087, 1993.
Solodin et al. "A novel series of amphiphilic imidazolinium compounds for in vitro and vivo gene delivery," Biochemistry 34:13537, 1995.
Spanjer and Scherphof, "Targeting of lactosylceramide liposomes to hepatocytes in vivo," Biochim Biophys ACTA, 734:40-47, 1983.
Templeton et al., "Improved DNA: liposome complexes for increased systemic delivery and gene expression," Nat. Biotechnol., 15:647-52, 1997.
Thierry et al. "Systematic gene therapy: biodistribution and long-term expression of a transgene in mice," Proc. Natl. Acad. Sci. USA, 92:9742, 1995.
Tsukamoto et al. "Gene transfer and expression in progeny after intravenous DNA injection into pregnant mice," Nature Genetics., 9:243, 1995.
Wong a al., "Appearance of β-lactamase activity in animal cells upon liposome mediated gene transfer," Gene, 10:87-94, 1980.
Yang and Huang, "Overcoming the inhibitory effect of serum on lipofection by increasing the charge ratio of cationic liposome to DNA," Gene Therapy, 4:950-960, 1997.
Zhu et al., "Systematic gene expression after intravenous DNA delivery into adult mice," Science, 261:209-211, 1993.
Xu, M. et al., "Gene Therapy with P53 and a Fragment of Thrombospondin I Inhbits Human Breast Cancer In Vivo," Mol Genet Matab 63, 103-109 (1998).

* cited by examiner

SEQUENCE LISTING

```
<160> NUMBER OF SEQ ID NOS: 2

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Arg Gly Asp
  1

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Arg Gly Asp Phe Val
  1               5
```

METHODS AND COMPOSITIONS FOR NON-VIRAL GENE THERAPY FOR TREATMENT OF HYPERPROLIFERATIVE DISEASES

The present application claims the benefit of U.S. Provisional Application Ser. No. 60/135,818 filed on May 24, 1999.

BACKGROUND OF THE INVENTION

A. Field of the Invention

The present invention relates generally to the fields of oncology and gene therapy. More particularly, it concerns the formulation of lipid based pharmaceuticals. In specific embodiments, it relates to lipid based non-viral formulations related to gene delivery for treating hyperproliferative diseases.

B. Description of Related Art

1. Gene Therapy

Gene therapy is an emerging field in biomedical research with a focus on the treatment of disease by the introduction of therapeutic recombinant nucleic acids into somatic cells of patients. Various clinical trials using gene therapies have been initiated and include the gene therapy of various cancers, AIDS, cystic fibrosis, adenosine deaminase deficiency, cardiovascular disease, Gaucher's disease, rheumatoid arthritis, and others. Currently, the preferred vehicle for the delivery of gene therapy agents is the adenovirus. Advantages in using adenovirus as a gene therapy agent are high transduction efficiency, infection of non-dividing cells, easy manipulation of its genome, and low probability of non-homologous recombination with the host genome. Adenoviral gene therapy strategies, however, suffer from many inherent problems including the potential for patient immune response, a possible inability to repeat administration of viral vectors, a difficulty in generating high viral titers, and the potential of infectious virus production. Non-viral delivery systems provide an alternative gene therapy vehicle that is devoid of one or more of these problems.

2. Lipid-Based Gene Transfer

Lipid-based non-viral formulations provide an alternative to adenoviral gene therapies. Although many cell culture studies have documented lipid-based non-viral gene transfer, systemic gene delivery via lipid-based formulations has been limited. A major limitation of non-viral lipid-based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use aerosolization, subcutaneous, intradermal, intratumoral, or intracranial injection to avoid the toxicity and stability problems associated with cationic lipids in the circulation. The interaction of liposomes and plasma proteins is largely responsible for the disparity between the efficiency of in vitro (Feigner et al., 1987) and in vivo gene transfer (Zhu et al., 1993; Philip et al., 1993; Solodin et al., 1995; Liu et al., 1995; Thierry et al., 1995; Tsukamoto et al., 1995; Aksentijevich et al., 1996).

Recent advances in liposome formulations have improved the efficiency of gene transfer in vivo (Templeton et al. 1997; WO 98/07408, incorporated herein by reference). A novel liposomal formulation composed of an equimolar ratio of 1,2-bis(oleoyloxy)-3-(trimethyl ammonio)propane (DOTAP) and cholesterol significantly enhances systemic in vivo gene transfer, approximately 150 fold. The DOTAP:cholesterol lipid formulation is said to form a unique structure termed a "sandwich liposome." This formulation is reported to "sandwich" DNA between an invaginated bilayer or "vase" structure. Beneficial characteristics of these liposomes include a positive to negative charge or p, colloidal stabilization by cholesterol, two-dimensional DNA packing and increased serum stability.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Liposomal encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

3. Cancer

Normal tissue homeostasis is a highly regulated process of cell proliferation and cell death. An imbalance of either cell proliferation or cell death can develop into a cancerous state (Solyanik et al., 1995; Stokke et al., 1997; Mumby and Walter, 1991; Natoli et al., 1998; Magi-Galluzzi et al., 1998). For example, cervical, kidney, lung, pancreatic, colorectal and brain cancer are just a few examples of the many cancers that can result (Erlandsson, 1998; Kolmel, 1998; Mangray and King, 1998; Gertig and Hunter, 1997; Mougin et al., 1998). In fact, the occurrence of cancer is so high that over 500,000 deaths per year are attributed to cancer in the United States alone.

The maintenance of cell proliferation and cell death is at least partially regulated by proto-oncogenes. A proto-oncogene can encode proteins that induce cellular proliferation (e.g., sis, erbB, src, ras and myc), proteins that inhibit cellular proliferation (e.g., Rb, p53, NF1 and WT1) or proteins that regulate programmed cell death (e.g., bcl-2) (Ochi et al., 1998; Johnson and Hamdy, 1998; Liebermann et al., 1998). However, genetic rearrangements or mutations to these proto-oncogenes, results in the conversion of a proto-oncogene into a potent cancer causing oncogene. Often, a single point mutation is enough to transform a proto-oncogene into an oncogene. For example, a mutation at codon 12 or 13 in the K-ras gene can convert the proto-oncogene into an oncogene.

Currently, there are few effective options for the treatment of many common cancer types. The course of treatment for a given individual depends on the diagnosis, the stage to which the disease has developed and factors such as age, sex and general health of the patient. The most conventional options of cancer treatment are surgery, radiation therapy and chemotherapy. Surgery plays a central role in the diagnosis and treatment of cancer. Typically, a surgical approach is required for biopsy and to remove cancerous growth. However, if the cancer has metastasized and is widespread, surgery is unlikely to result in a cure and an alternate approach must be taken. Radiation therapy, chemotherapy and immunotherapy are alternatives to surgical treatment of cancer (Mayer, 1998; Ohara, 1998; Ho et al., 1998). Radiation therapy involves a precise aiming of high energy radiation to destroy cancer cells and much like surgery, is mainly effective in the treatment of non-metastasized, localized cancer cells. Side effects of radiation therapy include skin irritation, difficulty swallowing, dry mouth, nausea, diarrhea, hair loss and loss of energy (Curran, 1998; Brizel, 1998).

Chemotherapy, the treatment of cancer with anti-cancer drugs, is another mode of cancer therapy. The effectiveness of a given anti-cancer drug therapy is often limited by the difficulty of achieving drug delivery throughout solid tumors (el-Kareh and Secomb, 1997). Chemotherapeutic strategies are based on tumor tissue growth, wherein the anti-cancer drug is targeted to the rapidly dividing cancer cells. Most chemotherapy approaches include the combination of more than one anti-cancer drug, which has proven to increase the response rate of a wide variety of cancers (U.S. Pat. No. 5,824,348; U.S. Pat. No. 5,633,016 and U.S. Pat. No. 5,798,339). A major side effect of chemotherapy drugs is that they also affect normal tissue cells, with the cells most likely to be affected being those that divide rapidly (e.g., bone marrow, gastrointestinal tract, reproductive system and hair follicles). Other toxic side effects of chemotherapy drugs are sores in the mouth, difficulty swallowing, dry mouth, nausea, diarrhea, vomiting, fatigue, bleeding, hair loss and infection. Other forms of chemotherapy can be used to treat non-cancerous hyperproliferative disorders. These include the use of conventional chemotherapeutics such as methotrexate and cyclophosphamide for hyperproliferative diseases such as rheumatoid arthritis and psoriasis. Chemotherapy for hyperproliferative diseases can also include immunosuppressive agents such as steroids, azathioprine, cyclosporine and immunomodulatory agents such as fumaric acid derivatives.

The lipid drug delivery can also be used in combination with phetadynamic therapy or in combination with retinoids, biological therapies such as monoclonal and cytokine antagonists (e.g., TNF-alpha receptor antagonist) or enzyme inhibitors such as difluromethyl or nithine. Inhibitors of matrix metalloproteinases could also be used in combination with the invention described (e.g., bromocriptin and butyrede).

Immunotherapy, a rapidly evolving area in cancer research, is yet another option for the treatment of certain types of cancers. For example, the immune system identifies tumor cells as being foreign and thus they are targeted for destruction by the immune system. Unfortunately, the response typically is not sufficient to prevent most tumor growths. However, recently there has been a focus in the area of immunotherapy to develop methods that augment or supplement the natural defense mechanism of the immune system. Examples of immunotherapies currently under investigation or in use are immune adjuvants (e.g., *Mycobacterium bovis*, *Plasmodium falciparum*, dinitrochlorobenzene and aromatic compounds) (U.S. Pat. No. 5,801,005; U.S. Pat. No. 5,739,169; Hui and Hashimoto, 1998; Christodoulides et al., 1998), cytokine therapy (e.g., interferons α, β and γ; IL-1, GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. No. 5,830,880 and U.S. Pat. No. 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311).

As mentioned above, proto-oncogenes play an important role in cancer biology. For example, Rb, p53, NF1 and WT1 tumor suppressors are essential for the maintenance of the non-tumorogenic phenotype of cells (reviewed by Soddu and Sacchi, 1998). Approximately 50% of all cancers have been found to be associated with mutations of the p53 gene, which result in the loss of p53 tumor suppressor properties (Levine et al., 1991; Vogelstein and Kinzler, 1992; Hartmann et al., 1996a; Hartmann et al., 1996b). The high incidence of mutations of the p53 gene in cancer has prompted many research groups to investigate p53 as a route of cancer treatment via gene transfer or replacement. The proto-oncogenes sis, erbB, src, ras and myc, encoding proteins that induce cellular proliferation, and the proto-oncogenes of the Bcl-2 family that regulate programmed cell death also play important roles in the non-tumorigenic phenotype of cells.

Lipid delivery of nucleic acids for gene transfer or replacement therapy may be used alone, or in combination with the above described treatments to provide a means to sensitize hyperproliferative and/or neoplastic cells to conventional therapies. Systemic delivery of nucleic acids will have the potential to target metastatic as well as solid tumor cancer and cancerous, pre-cancerous, and non-cancerous cells.

The optimization of lipid drug delivery by systemic administration would permit the treatment of hyperproliferative cells throughout the organism. Therefore, there exists a need for a pharmaceutical lipid formulation that is capable of efficient nucleic acid transfer for the treatment of hyperproliferative diseases. Further, lipid drug delivery may increase the efficiency of gene transfer to target cells. Moreover, the need exists for a stable, pharmaceutically acceptable lipid delivery vehicle that is capable of delivering pharmaceuticals, in particular nucleic acid based pharmaceuticals, for the treatment of hyperproliferative cells with altered expression of proto-oncogenes.

SUMMARY OF THE INVENTION

It is, therefore, an objective of the present invention to provide a pharmaceutically acceptable lipid formulation comprising DOTAP and at least one cholesterol or cholesterol derivative or cholesterol mixture in combination with a nucleic acid representing or encoding (a) an anti-proliferative protein or (b) an antisense molecule or a ribozyme that inhibits the expression of a growth-promoting protein for treating a subject with a hyperproliferative disease. It is contemplated that any of the formulations of the present invention may comprise an antisense molecule or ribozyme that inhibits the expression of a particular protein instead of a nucleic acid encoding an antisense molecule or ribozyme to a particular protein. It is further contemplated that any of the nucleic acids of the present invention may be under the control or operably linked to a promoter.

Additionally a dominant negative variant, a single chain antibody, or a decoy directed to an oncoprotein or growth-promoting protein can be delivered. The phrase "directed to" in the context of proteins and polypeptides "directed to" a targeted protein or polypeptide refer to the inhibition of activity, either directly or indirectly, of the targeted protein or polypeptide.

The formulation of a pharmaceutically acceptable lipid vehicle for the transfer of nucleic acids in the present invention comprises DOTAP and at least one cholesterol or cholesterol derivative or cholesterol mixture in combination with a nucleic acid representing or encoding an anti-proliferative protein or an antisense molecule or a ribozyme that inhibits the expression of growth-promoting protein. Additionally a dominant negative variant, a single chain antibody, or a decoy to an oncoprotein can also be delivered. Following administration of the formulation to a subject with a hyperproliferative disease, an expression construct comprising a therapeutic nucleic acid under the control of a promoter that is active in eukaryotic cells is transferred to cells via a lipid based vehicle. The therapeutic gene product may be expressed directly by the hyperproliferative cells, thereby stimulating a growth arrest or apoptic response. Additionally or alternatively, it may be expressed by cells in the vicinity of the hyperproliferative cells to indirectly modulate their hyperproliferation. An example would be transfer of antiproliferative or apoptotic genes to tumor vascular cells, thus leading to an anti-angiogenic process; another example involves a bystander effect in which a non-hyperproliferative cell expresses and secretes the therapeutic gene product such that nearby cells that do not express the product are similarly affected.

In certain preferred embodiments, the pharmaceutically acceptable lipid formulation includes DOTAP in a concentration ranging from 1 to 8 mM. In more preferred embodiments, the pharmaceutically acceptable lipid is a formulation comprising DOTAP in a concentration ranging from 2 to 7 mM. In still more preferred embodiments, the pharmaceutically acceptable lipid is a formulation comprising DOTAP in a concentration ranging from 3 to 6 mM. Most preferably, the pharmaceutically acceptable lipid is a formulation comprising DOTAP in a concentration of about 4 to 5 mM.

In certain preferred embodiments, the pharmaceutically acceptable lipid formulation includes cholesterol or cholesterol derivative or cholesterol mixture in a concentration ranging from 1 to 8 mM. In more preferred embodiments, the cholesterol or cholesterol derivative or cholesterol mixture is included in a concentration ranging from 2 to 7 mM. In still more preferred embodiments, the pharmaceutically acceptable lipid is a formulation comprising the cholesterol or cholesterol derivative or cholesterol mixture in a concentration ranging from 3 to 6 mM. Most preferably the pharmaceutically acceptable lipid is a formulation comprising the cholesterol or cholesterol derivative or cholesterol mixture in a concentration of about 4 to 5 mM.

Preferably, the DOTAP and cholesterol or cholesterol derivative or cholesterol mixture are included in a molar ratio of from about 3:1 to about 1:3, more preferably 2:1 to about 1:2, and most preferably about 1:1. It is also contemplated that the lipid formulation or liposome is extruded one or more times.

In preferred embodiments, the therapeutic nucleic acid is an oncogene, wherein the oncogene is a gene encoding a tumor suppressor, tumor associated protein, growth factor, growth-factor receptor, signal transducer, hormone, cell cycle regulator, nuclear factor, transcription factor or apoptotic factor. The therapeutic nucleic acid may encode a fusion protein that represents one or more of these species. The therapeutic nucleic acid may encode a polypeptide mimetic of one or more of these species. The therapeutic nucleic acid may be an "anti-oncogene," i.e., a nucleic acid that produces a molecule that is able to abrogate or downregulate the activity of proteins involved in increased cell proliferation, such as oncogenes or oncoproteins. Such molecules include antisense nucleic acids, ribozymes, and genes encoding single chain antibodies directed against oncoproteins, decoys for oncoproteins and dominant negative forms of oncoproteins. The therapeutic nucleic acids will also include therapeutic peptide nucleic acids and complexes of therapeutic nucleic acids with proteins such as transcription factors or polymerases. It is envisioned that therapeutic nucleic acids can be used in various combinations for the treatment of hyperproliferative diseases. Combinations of therapeutic nucleic acids can be delivered by a single lipid formulation or by administration of multiple lipid formulations. These combinations may include the genes for immunomodulatory molecules such as IL-2, F42K, GM-CSF, and/or 11-12. Additional genes include immunomodulatory antagonists (e.g., TNF-alpha receptor antagonists).

In preferred embodiments, the anti-proliferative protein is a tumor suppressor protein, wherein the tumor suppressor is Rb, p53, p14, p15, p16, p19, INK4c, p21, p27, p73, a p16-p27 fusion, a p21-p27 fusion, p56$^{RB}$, E2F-1, NOEY2, DCC, APC, NF-1, NF-2, PTEN, FHIT, C-CAM, E-cadherin, MEN-I, MEN-II, ZAC1, VHL, FCC, MCC, PMS1, PMS2, MLH-1, MSH-2, DPC4, BRCA1, BRCA2, MDA-7, DBCCR-1, p57, Barx2, E1A, apoptin, or WT-I. In particularly preferred embodiments, the tumor suppressor is p53. An "anti-proliferative protein" refers to a protein or polypeptide that is capable of reducing or inhibiting the growth, growth rate, or proliferation of a cell, including a hyperproliferative cell or tumor cell. Anti-proliferative proteins include proteins that promote apoptosis.

In certain embodiments of the invention, an antisense molecule or ribozyme directed to a growth factor receptor encoding molecule. In further embodiments, an anti-proliferative protein is a single chain antibody, a decoy, or a dominant negative and is directed to a growth factor or growth factor receptor protein. In preferred embodiments, the growth factor receptor is FMS, ERBB/HER, ERBB-2/NEU/HER-2, ERBA, TGF-β receptor, PDGF receptor, MET, KIT or TRK.

In another embodiment, the anti-proliferative protein is a single chain antibody, a decoy, or a dominant negative directed to a signal transducer protein or an antisense molecule or ribozyme directed to a signal transducer protein. In preferred embodiments, the signal transducer protein is SRC, ABL, RAS, AKT/PKB, RSK-1, RSK-2, RSK-3, RSK-B, PRAD, LCK, or ATM.

In yet another embodiment of the invention, the anti-proliferative protein is a single chain antibody, a decoy, or a dominant negative directed to a transcription factor protein or an antisense molecule or ribozyme directed to a transcription factor protein. In preferred embodiments, the transcription factor protein is JUN, FOS, MYC, BRCA1, BRCA2, ERBA, ETS, EVII, MYB, HMGI-C, HMGG/LIM, SKI, VHL, WT1, CEBP-α, NFκB, IκB, GL1, or REL.

Additional molecules that can be used in association with the invention are molecules that upregulate cell surface receptors for TRAIL, FAS ligand, and/or other surface receptors for apoptosis inducing ligands or the ligands themselves, angiogensis inhibitors, and anti-thrombic agents or genes.

In yet another embodiment, the anti-proliferative protein is a single chain antibody, a decoy, or a dominant negative directed to a growth factor protein or an antisense molecule or ribozyme directed to a growth factor protein. In preferred embodiments, the growth factor protein is SIS, HST, INT-1/WT1, or INT-2.

In certain embodiments, the anti-proliferative protein is an apoptotic factor protein, wherein the apoptotic factor protein is Bax, Bak, Bim, Bik, Bcl-xL, Bcl-xS, Bid, Bad, Bcl-2, Harakiri, or an ICE protease.

In certain embodiments, the anti-proliferative protein is a single chain antibody, a decoy, or a dominant negative directed to a tumor associated protein or an antisense molecule or ribozyme directed to a tumor-associated protein, wherein the tumor associated protein is CEA, mucin, MAGE, or GAGE.

In certain preferred embodiments, the pharmaceutically acceptable lipid formulation further comprises a targeting moiety. More preferred embodiments include a targeting moiety that is a peptide, a ligand, or an antibody. In still more preferred embodiments, the peptide includes a RGD or GFE sequence. In certain preferred embodiments the peptide is from 3 to 30 amino acids in length, more preferred is from 3 to 20 amino acids in length, and most preferred is from 4 to 10 amino acids in length. More preferably, the peptide is a cyclic peptide.

In certain preferred embodiments, the targeting moiety comprises a ligand which is a substrate for a cell surface protein. In further preferred embodiments, the ligand is a substrate for integrins, proteoglycans, glycoproteins, receptors, and transporters. In still further preferred embodiments, the targeting moiety comprises an antibody that binds to a cell surface protein. Most preferably, the antibody is an antibody to the Her-1 receptor.

The therapeutic nucleic acid may be linear, branched, or circular. It may be single- double-, or triple-stranded or a mixture. In certain embodiments, the therapeutic nucleic acid contains a promoter. The promoter may be isolated from any natural source, may be synthetic, or may be chimeric, i.e., pieces of it may come from multiple sources including synthesis. In certain preferred embodiments, the promoter is CMV IE, VEGF, CEA, dectin-1, dectin-2, human CD11c, F4/80, SM22-alpha or MHC class II. More preferably the promoter is CMV IE. In another preferred embodiment the expression vector further comprises a polyadenylation signal. The therapeutic nucleic acid may also contain a transcriptional enhancer. The enhancer may be isolated from any natural source, may be totally synthetic, or may be chimeric, i.e., pieces of it may come from multiple sources including synthesis. In certain preferred embodiments the enhancer is derived from CMV. The therapeutic nucleic acid may also contain an intron. The intron may be isolated from any natural source, maybe synthetic, or may be chimeric, i.e., pieces of it may come from multiple sources including synthesis. In certain preferred embodiments, the intron is derived from CMV. The therapeutic nucleic acid may be non-replicating, conditionally-replicating, or replicating in the host cell. The therapeutic nucleic acid may include protein secretory signals or translocation sequences that permit its protein product to be passed from one cell to another cell or to the circulation.

It is contemplated, of this present invention, a method of treating hyperproliferative disorders comprising administering an effective amount of the lipid formulation to a patient in need of anti-proliferative therapy. In certain preferred embodiments, the hyperproliferative disease of interest can be any disorder in which the normal cell homeostasis is altered and an imbalance of cell proliferation and cell death leads to a dysregulated cellular proliferation. The aforementioned hyperproliferation can lead to neoplastic, pre-neoplastic and non-neoplastic disease states. It is further contemplated that a hyperproliferative neoplastic disease is cancer, wherein the cancer is derived from the dysregulated proliferation of a somatic, stem or germ cell from various tissues. Examples of cancer include, but are not limited to lung, head, neck, breast, pancreatic, prostate, renal, bone, testicular, cervical, gastrointestinal, lymphoma, ovarian, leukemia, myeloma, esophageal, skin, thyroid, liver, brain, colorectal and bladder cancer.

In certain preferred embodiments, the hyperproliferative disease is non-cancerous. In further preferred embodiments, non-cancerous hyperproliferative diseases include but are not limited to rheumatoid arthritis, cardiac disease, adenoma, leiomyoma, lipoma, hemangioma, fibroma, inflammatory bowel disease, osteo-arthritis, and psoriasis. It is still further contemplated that the hyperproliferative disorder is vascular occlusion disease, more preferably vascular restenosis.

Also contemplated in the present invention are various treatment methods of contacting the target cells with a pharmaceutically acceptable lipid formulation. Included in these treatment methods is intravenous, intradermal, intraarterial, intra-peritoneal, intralesional, intracranial, intraarticular, intraprostatic, intrapleural, intratracheal, intramuscular, intranasal, intravesicular, intravitreal, intravaginal, rectal and intratumoral injection or administration; infusion, continuous infusion; localized perfusion; bathing target cells directly or via a catheter; topical administration; or transdermal absorption; and/or aerosolization, instillation. In certain preferred embodiments, the formulation is administered to the tumor bed prior to or after resection of the tumor.

It is envisioned that treatments will be either single or multiple administrations via one or a combination of the aforementioned treatment methods. Treatments will be administered directly, locally, regionally, and/or systemically in order to contact the target cells.

It is contemplated, of the present invention, that the formulation is administered to the patient before, during or after chemotherapy, surgery or radiotherapy. Preferably the lipid formulation is administered less than 72 hours prior to chemotherapy, surgery or radiotherapy. More preferably the lipid formulation is administered less than 24 hours prior to chemotherapy, surgery or radiotherapy. In another preferred embodiment the lipid formulation is administered less than 72 hours after chemotherapy, surgery or radiotherapy. More preferably the lipid formulation is administered less than 24 hours after chemotherapy, surgery or radiotherapy. It further contemplated that the invention may be practiced as a therapy in and of itself.

Disseminated hyperproliferative diseases are commonly treated with chemotherapeutic agents. Characteristics of chemotherapeutic agents limit the time and magnitude of patient exposure. It is contemplated, of the present invention, that the effectiveness of chemotherapy can be enhanced by combining chemotherapeutic and lipid formulation treatments. Combination chemotherapies include, for example, cisplatin, carboplatin, procarbizine, mechlorethamine, cyclophosphamide, camptothecin, ifosfamide, melphalan, chlorombucil, bisulfan, nitrosurea, dactinomycin, daunorubicin, doxorubicin, bleomycin, plicomycin, mitomycin, etoposide, tamoxifen, taxol, transplatinum, 5-fluorouracil, vincristin, vinblastin, taxotere, and methotrexate or any analog or derivative variant thereof.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifi-

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 1A. Subcutaneous H1299 tumor-bearing mice were divided into three groups (8 animals/group) and treated daily for a total of six doses (100 µg/dose), as follows: no treatment (♦), p53 plasmid DNA (□) and DOTAP:Chol-p53 DNA:liposome complex (■) (FIG. 1A); no treatment (♦), DOTAP:Chol-pAd DNA: liposome complex (□) and DOTAP:Chol-p53 DNA:liposome complex (■) (FIG. 1B). Tumors were measured using calipers and statistical significance calculated using Student's t test. Each time point represents the average mean tumor volume for each group.) Bars represent standard error. FIG. 1B. p53 gene expression and apoptotic cell death following DOTAP:Chol-p53 DNA:liposome treatment. Subcutaneous H1299 tumors from animals receiving no treatment, p53 plasmid, or the DOTAP:Chol-p53 DNA: liposome complex were harvested at 48 hours after treatment. p53 protein production was analyzed by immunohistochemistry and apoptotic cell death by TUNEL staining. The percentage of cells producing the p53 protein (39%) (FIG. 1C) and undergoing apoptotic cell death (32%) (FIG. 1D) in tumors receiving the DOTAP:Chol-p53 DNA:liposome complex was significant ($p=0.001$) versus the percentage of cells in the no treatment and p53 plasmid treatment groups. FIGS. 1D-F. Therapeutic effect of the DOTAP:Chol-FHIT DNA:liposome complex on lung tumor xenografts. Subcutaneous H1299 and A549 tumor-bearing nude mice were divided into four groups (7 animals/group) and treated daily for a total of six doses (100 µg/dose), as follows: no treatment, FHIT plasmid DNA, the DOTAP:Chol-CAT DNA:liposome complex, and DOTAP:Chol-FHIT DNA: liposome complex. H1299 tumor treatments (FIG. 1E), and A549 tumor treatments (FIG. 1F). Tumor growth was significantly inhibited in H1299 ($p=0.02$) and A549 ($p=0.001$) tumor-bearing animals treated with the DOTAP:Chol-FHIT DNA:liposome complex. Bars denote standard error.

FIG. 2A. Inhibition of H1299 lung metastases following DOTAP:Chol-p53 DNA:liposome complex treatment. H1299 lung tumor-bearing SCID/Beige mice were either not treated or treated daily for a total of six doses (50 µg/dose) with p53 plasmid DNA, the DOTAP:DOPE-p53 DNA:liposome complex, the nonextruded DOTAP:Chol-p53 DNA:liposome complex, the extruded DOTAP:Chol-CAT DNA:liposome complex, or the extruded DOTAP: Chol-p53 DNA:liposome complex. Each group was comprised of eight animals. Metastatic tumor growth ($p=0.001$) was significantly inhibited in mice treated with extruded DOTAP:Chol-p53 DNA:liposome complex as compared with growth in the other groups (FIG. 2A). FIG. 2B. Inhibition of A549 lung metastases following DOTAP: Chol-p53 DNA:liposome complex treatment. A599 lung tumor-bearing nu/nu mice were either not treated or treated daily for a total of six doses (50 µg/dose) with the extruded DOTAP:Chol-CAT DNA:liposome complex, or the extruded DOTAP:Chol-p53 DNA:liposome complex. Each group was comprised of eight animals. Metastatic tumor growth ($p=0.001$) was significantly inhibited in mice treated with extruded DOTAP:Chol-p53 DNA:liposome complex as compared with growth in the two control groups. FIG. 2C. Inhibition of A549 lung metastases following DOTAP:Chol-FHIT DNA:liposome complex treatment. A549 lung tumor-bearing nu/nu mice were divided into four groups and treated as follows: no treatment, treatment with FHIT plasmid DNA, treatment with DOTAP:Chol-CAT DNA:liposome complex, and treatment with DOTAP:Chol-FHIT DNA:liposome complex daily for a total of six doses (50 µg/dose). Each group comprised of six animals. There was significant reduction in the number of lung tumor ($p=0.007$) in mice treated with DOTAP:Chol-FHIT DNA:liposome complex. In all the experiments, lungs were harvested 2 weeks after the last treatment and metastases counted without knowledge of the treatment group. Bars denote standard error.

DESCRIPTION OF ILLUSTRATIVE EMBODIMENTS

Figures 1A, 1B:
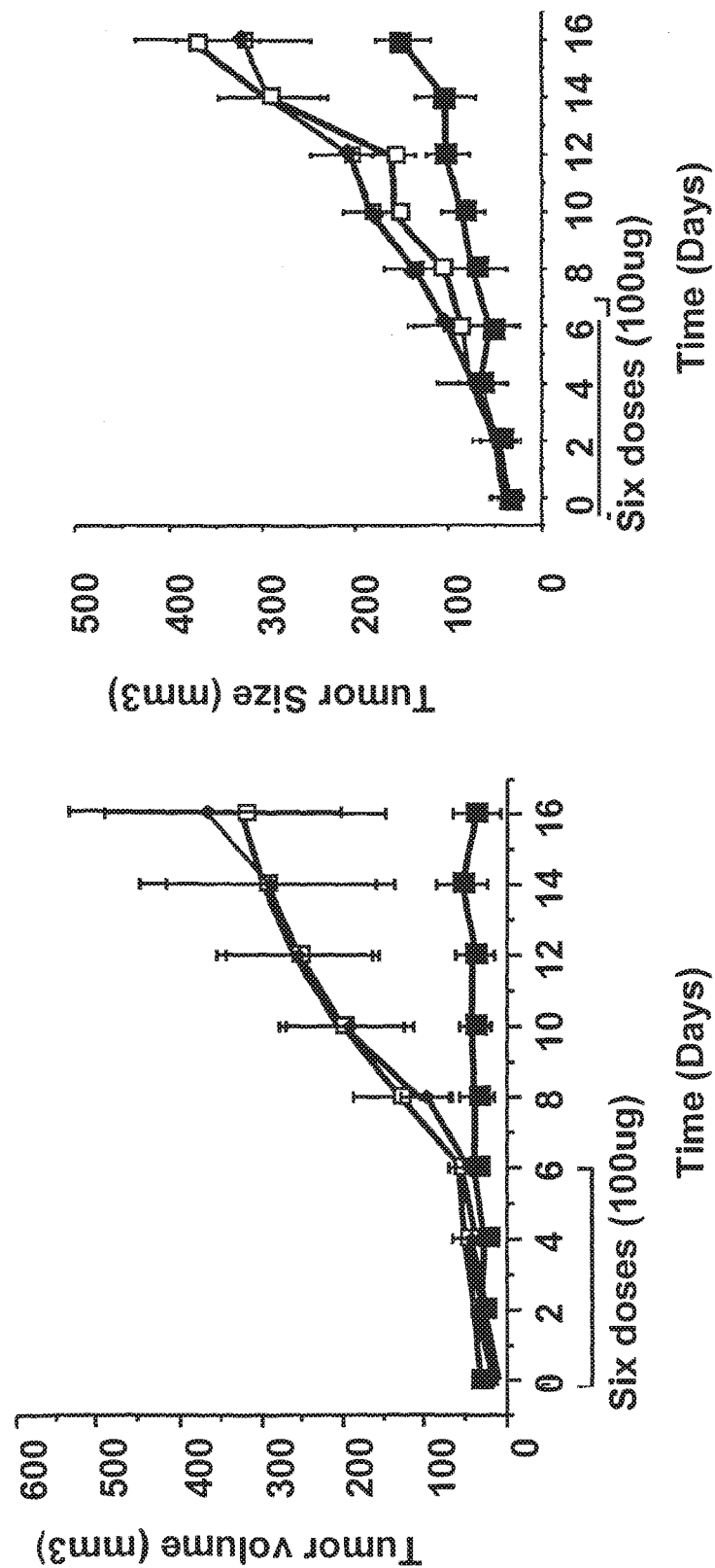
FIGS. 1A-F. Therapeutic effect of p53 and FHIT complexed to DOTAP:Chol liposome treatment on subcutaneous human lung cancer xenografts.

The present invention contemplates the formulation of a pharmaceutically acceptable lipid, comprising DOTAP and cholesterol, a cholesterol derivative or a cholesterol mixture, and a nucleic acid encoding an anti-proliferative protein, antisense or ribozyme for delivery of the nucleic acid into hyperproliferative cells or into cells near the hyperproliferative cells. The treatment of such a hyperproliferative disease in one embodiment involves the intravenous administration of a lipid and a p53 expression construct complex to hyperproliferative cells, which subsequently express the p53 wild-type protein. The hyperproliferative cells then express p53, resulting in the stasis, destruction or lysis of hyperproliferative cells.

A. Hyperproliferative Disease

A variety of hyperproliferative diseases can be treated according to the methods of the present invention. Some of the hyperproliferative diseases contemplated for treatment in the present invention are psoriasis, rheumatoid arthritis (RA), vascular occlusion, including vascular restenosis, inflammatory bowel disease (MD), osteoarthritis (OA) and pre-neoplastic lesions in the mouth, prostate, breast, lung, etc. Also included are adenoma, leiomyoma, lipoma, hemangioma, and fibroma. The present invention has important ramifications particularly with respect to one hyperproliferative disease: cancer.

Cancer has become one of the leading causes of death in the Western world, second only behind heart disease. Current estimates project that one person in three in the U.S. will develop cancer, and that one person in five will die from cancer. Cancers can be viewed as altered cells that have lost the normal growth-regulating mechanisms.

There are currently three major categories of oncogenes, reflecting their different activities. One category of oncogenes encode proteins that induce cellular proliferation. A second category of oncogenes, called tumor-suppressor genes or anti-oncogenes, functions to inhibit excessive cellular proliferation. The third category of oncogenes either blocks or induces apoptosis by encoding proteins that regulate programmed cell death. Members within each of these categories can be toxic when expressed in cells. This toxicity may be prohibitive during the production of viral based pharmaceuticals in mammalian systems. The inherent toxicity of these nucleic acids is not an issue in regards to the manufacturing processes of the present invention. It is envisioned, of the present invention, to be used in the manufacturing of said toxic nucleic acids. This does not limit the present invention to the manufacture of the toxic nucleic acids as less toxic or non-toxic nucleic acids may be manufactured as well.

In some embodiments, the treatment of a wide variety of cancerous states or tissue/organ types is within the scope of the invention, for example, melanoma, non-small cell lung, small-cell lung, lung, hepatocarcinoma, retinoblastoma, astrocytoma, glioblastoma, leukemia, blood, brain, skin, eye, tongue, gum, neuroblastoma, head, neck, breast, pancreatic, prostate, renal, bone, testicular, ovarian, mesothelioma, cervical, gastrointestinal, lymphoma, brain, colon or bladder. In still more preferred embodiments, the hyperproliferative disease being treated according to the present invention is rheumatoid arthritis, inflammatory bowel disease, osteoarthritis, leiomyomas, ademonas, lipomas, hemangiomas, fibromas, vascular occlusion, restenosis, atherosclerosis, pre-neoplastic lesions, carcinoma in situ, oral hairy leukoplakia or psoriasis.

In one embodiment of the present invention, the treatment of hyperproliferative disease involves the intravenous administration of a therapeutic nucleic acid expression construct to treat hyperproliferative cells. It is contemplated that the hyperproliferative cells will express the nucleic acid, thus restoring a missing function, supplementing an existing function, reducing a proliferative function, or adding a new protein that results in the growth arrest, destruction or lysis of hyperproliferative cells; such a nucleic acid would encode an anti-proliferative protein. An anti-proliferative polypeptide or protein is one that reduces or inhibits the growth, proliferation, or growth rate of a cell, or one that promotes or increases apoptosis of a cell. Alternatively, in other embodiments of the invention described below, an antisense molecule or ribozyme that inhibits the expression of a growth promoting polypeptide may be used to treat a hyperproliferative disease. A growth-promoting protein or polypeptide increases or promotes the growth rate, proliferation, or growth of a cell. It is contemplated that a nucleic acid molecule encoding such an antisense or ribozyme may be employed as well. The three major categories of oncogenes are discussed below and listed in Table 1.

1. Inducers of Cellular Proliferation

The proteins that induce or promote cellular proliferation (growth) fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally occurring oncogenic growth factor. In one embodiment of the present invention, it is contemplated that antisense mRNA, or a ribozyme, directed to a particular inducer of cellular proliferation (growth-promoting protein) is used to prevent expression of the inducer of cellular proliferation.

The proteins fins, erbA, erbB and neu are growth factor receptors. Mutations to these receptors result in loss of regulatable function. For example, a point mutation affecting the transmembrane domain of the neu receptor protein results in the neu oncogene. The erbA oncogene is derived from the intracellular receptor for thyroid hormone. The modified oncogenic erbA receptor is believed to compete with the endogenous thyroid hormone receptor, causing uncontrolled growth.

The largest class of oncogenes is the signal transducing proteins (e.g., src, abl and ras). The protein src, is a cytoplasmic protein-tyrosine kinase, and its transformation from proto-oncogene to oncogene in some cases results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins jun, fos and myc are proteins that directly exert their effects on nuclear functions as transcription factors. Table 1 lists a variety of the oncogenes described in this section and many of those not described.

2. Inhibitors of Cellular Proliferation

The tumor suppressor oncogenes function to inhibit excessive cellular proliferation (i.e., anti-proliferative protein). The inactivation of these genes destroys or reduces their inhibitory activity, resulting in unregulated proliferation. Thus, wild-type version of these tumor suppressors inhibit proliferation, and consequently are anti-proliferative. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations that are minute by comparison with transformed cells or tumor tissue.

Wild-type p53 is recognized as an important growth regulator in many cell types. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the $G_1$ phase. The activity of this enzyme may be to phosphorylate Rb at late $G_1$. The activity of CDK4 is controlled by an activating subunit, D-type cyclin, and by an inhibitory subunit, the p16$^{INK4}$. p16$^{INK4}$ has been biochemically characterized as a protein that specifically binds to and inhibits CDK4, and thus may regulate Rb phosphorylation (Serrano et al., 1993; Serrano et al., 1995). Since the p16' protein is a CDK4 inhibitor (Serrano, 1993), deletion of this gene may increase the activity of CDK4, resulting in hyperphosphorylation of the Rb protein. p16 also is known to regulate the function of CDK6.

p16$^{INK4}$ belongs to a newly described class of CDK-inhibitory proteins that also includes p16$^B$, p21$^{WAF1}$, p57$^{KIP2}$ and p27$^{KIP1}$. The p16$^{INK4}$ gene maps to 9p21, a chromosome region frequently deleted in many tumor types. Homozygous deletions and mutations of the p16$^{INK4}$ gene are frequent in human tumor cell lines. This evidence suggests that the p16$^{INK4}$ gene is a tumor suppressor gene. This interpretation has been challenged, however, by the observation that the frequency of the p16$^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type p16$^{INK4}$ function by transfection with a plasmid expression vector reduced colony formation by some human cancer cell lines (Okamoto, 1994; Arap, 1995).

C-CAM is expressed in virtually all epithelial cells (Odin and Obrink, 1987). C-CAM, with an apparent molecular weight of 105 kDa, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993) demonstrated that the first Ig domain of C-CAM is critical for cell adhesive activity.

Cell adhesion molecules, or CAMs are known to be involved in a complex network of molecular interactions that regulate organ development and cell differentiation (Edelman, 1985). Recent data indicate that aberrant expression of CAMs may be involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$, integrin by gene transfer can reduce tumorigenicity of Chinese hamster ovary cells in vivo. C-CAM now has been shown to suppress tumor growth in vitro and in vivo.

Other tumor suppressors that may be employed according to the present invention include p14, p15, p19, GAX, p56$^{RB}$, INK4c, RB, APC, FHIT, DCC, NF-1, NF-2, WT-1, MEN-I, MEN-II, zac1, p73, VHL, MMAC1, mda-7, DBCCR-1, FCC and MCC (see Table 1).

3. Regulators of Programmed Cell Death

Apoptosis, or programmed cell death, is an essential occurring process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins that can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., Bcl$_{xL}$, Bcl$_W$, Mcl-1, A1, Bfl-1) or counteract Bcl-2 function and promote cell death (e.g., Bax, Bak, Bik, Bim, Bid, Bad, Harakiri, Bcl$_{XS}$). Proteins that promote cell death are antiproliferative proteins; conversely, cells that suppress apoptosis are growth-promoting proteins.

TABLE 1

| ONCOGENES | | | |
| --- | --- | --- | --- |
| Gene | Source | Human Disease | Function |
| Growth Factors | | | |
| HST/KS | Transfection | | FGF family member |
| INT-2 | MMTV promoter Insertion | | FGF family member |
| INT1/WNT1 | MMTV promoter Insertion | | Factor-like |
| SIS | Simian sarcoma virus | | PDGF B |
| Receptor Tyrosine Kinases | | | |
| ERBB/HER | Avian erythroblastosis virus; ALV promoter insertion; amplified human tumors | Amplified, deleted squamous cell cancer; glioblastoma | EGF/TGF-α/ amphiregulin/ hetacellulin receptor |
| ERBB-2/NEU/HER-2 | Transfected from rat Glioblatoms | Amplified breast, ovarian, gastric cancers | Regulated by NDF/ heregulin and EGF-related factors |
| FMS | SM feline sarcoma virus | | CSF-1 receptor |

TABLE 1-continued

| | ONCOGENES | | |
|---|---|---|---|
| Gene | Source | Human Disease | Function |
| KIT | HZ feline sarcoma virus | | MGF/Steel receptor hematopoieis |
| TRK | Transfection from human colon cancer | | NGF (nerve growth factor) receptor |
| MET | Transfection from human osteosarcoma | | Scatter factor/HGF receptor |
| RET | Translocations and point mutations | Sporadic thyroid cancer; familial medullary thyroid cancer; multiple endocrine neoplasias 2A and 2B | Orphan receptor Tyr kinase |
| ROS | URII avian sarcoma Virus | | Orphan receptor Tyr kinase |
| PDGF receptor | Translocation | Chronic myclomonocytic leukemia | TEL(ETS-like transcription factor)/PDGF receptor gene fusion |
| TGF-β receptor | | Colon carcinoma mismatch mutation target | |
| | NONRECEPTOR TYROSINE KINASES | | |
| ABL. | Abelson Mul. V | Chronic myelogenous leukemia translocation with BCR | Interact with RB, RNA polymerase, CRK, CBL |
| FPS/FES | Avian Fujinami SV; GA FeSV | | |
| LCK | Mul. V (murine leukemia virus) promoter insertion | | Src family; T cell signaling; interacts CD4/CD8 T cells |
| SRC | Avian Rous sarcoma Virus | | Membrane-associated Tyr kinase with signaling function; activated by receptor kinases |
| YES | Avian Y73 virus | | Src family; signaling |
| | SER/THR PROTEIN KINASES | | |
| AKT | AKT8 murine retrovirus | | Regulated by PI(3)K?; regulate 70-kd S6 k? |
| MOS | Maloney murine SV | | GVBD; cystostatic factor; MAP kinase kinase |
| PIM-1 | Promoter insertion Mouse | | |
| RAF/MIL | 3611 murine SV; MH2 avian SV | | Signaling in RAS pathway |
| | MISCELLANEOUS CELL SURFACE | | |
| APC | Tumor suppressor | Colon cancer | Interacts with catenins |
| DCC | Tumor suppressor | Colon cancer | CAM domains |
| E-cadherin | Candidate tumor Suppressor | Breast cancer | Extracellular homotypic binding; intracellular interacts with catenins |
| PTC/NBCCS | Tumor suppressor and *Drosophilia* homology | Nevoid basal cell cancer syndrome (Gorline syndrome) | 12 transmembrane domain; signals through Gli homogue CI to antagonize hedgehog pathway |
| TAN-1 Notch homologue | Translocation | T-ALI. | Signaling? |
| | MISCELLANEOUS SIGNALING | | |
| BCL-2 | Translocation | B-cell lymphoma | Apoptosis |
| CBL | Mu Cas NS-1 V | | Tyrosine-phosphorylated RING finger interact Abl |
| CRK | CT1010 ASV | | Adapted SH2/SH3 interact Abl |
| DPC4 | Tumor suppressor | Pancreatic cancer | TGF-β-related signaling pathway |
| MAS | Transfection and Tumorigenicity | | Possible angiotensin receptor |
| NCK | | | Adaptor SH2/SH3 |

TABLE 1-continued

ONCOGENES

| Gene | Source | Human Disease | Function |
|---|---|---|---|
| GUANINE NUCLEOTIDE EXCHANGERS AND BINDING PROTEINS[3] | | | |
| BCR | | Translocated with ABL in CML | Exchanger; protein kinase |
| DBL | Transfection | | Exchanger |
| GSP | | | |
| NF-1 | Hereditary tumor Suppressor | Tumor suppressor neurofibromatosis | RAS GAP |
| OST | Transfection | | Exchanger |
| Harvey-Kirsten, N-RAS | HaRat SV; Ki RaSV; Balb-MoMuSV; Transfection | Point mutations in many human tumors | Signal cascade |
| VAV | Transfection | | S112/S113; exchanger |
| NUCLEAR PROTEINS AND TRANSCRIPTION FACTORS | | | |
| BRCA1 | Heritable suppressor | Mammary cancer/ovarian cancer | Localization unsettled |
| BRCA2 | Heritable suppressor | Mammary cancer | Function unknown |
| ERBA | Avian erythroblastosis Virus | | thyroid hormone receptor (transcription) |
| ETS | Avian E26 virus | | DNA binding |
| EVII | MuLV promotor insertion | AML | Transcription factor |
| FOS | FB1/FBR murine osteosarcoma viruses | | 1 transcription factor with c-JUN |
| GLI | Amplified glioma | Glioma | Zinc finger; cubitus interruptus homologue is in hedgehog signaling pathway; inhibitory link PTC and hedgehog |
| HMGG/LIM | Translocation t(3:12) t(12:15) | Lipoma | Gene fusions high mobility group HMGI-C (XT-hook) and transcription factor LIM or acidic domain |
| JUN | ASV-17 | | Transcription factor AP-1 with FOS |
| MLL/VHRX + ELI/MEN | Translocation/fusion ELL with MLL trithorax-like gene | Acute myeloid leukemia | Gene fusion of DNA-binding and methyl transferase MLL with ELI RNA pol II elongation factor |
| MYB | Avian myeloblastosis Virus | | DNA binding |
| MYC | Avian MC29; translocation B-cell lymphomas; promoter insertion avian leukosis virus | Burkitt's lymphoma | DNA binding with MAX partner; cyclin regulation; interact RB?; regulate apoptosis? |
| N-MYC | Amplified | Neuroblastoma | |
| L-MYC | | Lung cancer | |
| REL | Avian Retriculoendotheliosis virus | | NF-κB family transcription factor |
| SKI | Avian SKV770 Retrovirus | | Transcription factor |
| VHL | Heritable suppressor | Von Hippel-Landau syndrome | Negative regulator or elongin; transcriptional elongation complex |
| WT-1 | | Wilm's tumor | Transcription factor |
| CELL CYCLE/DNA DAMAGE RESPONSE | | | |
| ATM | Hereditary disorder | Ataxia-telangiectasia | Protein/lipid kinase homology; DNA damage response upstream in P53 pathway |
| BCL-2 | Translocation | Follicular lymphoma | Apoptosis |
| FACC | Point mutation | Fanconi's anemia group C (predisposition leukemia | |
| FHIT | Fragile site 3p14.2 | Lung carcinoma | Histidine triad-related diadenosine 5',3''''-$P^1.p^4$ tetraphosphate asymmetric hydrolase |

TABLE 1-continued

ONCOGENES

| Gene | Source | Human Disease | Function |
| --- | --- | --- | --- |
| hMLI/MutL | | HNPCC | Mismatch repair; MutL homologue |
| hMSH2/MutS | | HNPCC | Mismatch repair; MutS homologue |
| hPMS1 | | HNPCC | Mismatch repair; MutL homologue |
| hPMS2 | | HNPCC | Mismatch repair; MutL homologue |
| INK4/MTS1 | Adjacent INK-4B at 9p21; CDK complexes | Candidate MTS1 suppressor and MLM melanoma gene | p16 CDK inhibitor |
| INK4B/MTS2 | | Candidate suppressor | p15 CDK inhibitor |
| MDM-2 | Amplified | Sarcoma | Negative regulator p53 |
| p53 | Association with SV40 T antigen | Mutated >50% human tumors, including hereditary Li-Fraumeni syndrome | Transcription factor; checkpoint control; apoptosis |
| PRAD1/BCL1 | Translocation with parathyroid hormone or IgG | Parathyroid adenoma; B-CLL | Cyclin D |
| RB | Hereditary Retinoblastoma; association with many DNA virus tumor Antigens | Retinoblastoma; osteosarcoma; breast cancer; other sporadic cancers | Interact cyclin/cdk; regulate E2F transcription factor |
| XPA | | xeroderma pigmentosum; skin cancer predisposition | Excision repair; photo-product recognition; zinc finger |

4. Non-Cancer Hyperproliferative Diseases

In one embodiment of the present invention, it is contemplated that non-cancer hyperproliferative diseases may be treated by administering a therapeutic nucleic acid expression construct capable of eliciting an anti-hyperproliferative response. Some of the hyperproliferative diseases contemplated for treatment in the present invention are psoriasis, rheumatoid arthritis (RA), inflammatory bowel disease (IBD), osteoarthritis (OA), adenoma, fibroma, hemangioma, lipoma, and pre-neoplastic lesions in the lung.

B. Liposome Mediated Transformation

Liposomes are vesicular structures characterized by a lipid bilayer and an inner aqueous medium. Multilamellar liposomes have multiple lipid layers separated by aqueous medium. They form spontaneously when lipids are suspended in an excess of aqueous solution. The lipid components undergo self-rearrangement before the formation of structures that entrap water and dissolved solutes between the lipid bilayers (Ghosh and Bachhawat, 1991). Lipophilic molecules or molecules with lipophilic regions may also dissolve in or associate with the lipid bilayer.

1. Liposome Preparation

The present invention relates to liposomes of a specific composition which form a stable structure and are efficient carriers of biologically active agents. The liposomes are capable of carrying biologically active nucleic acids, such that the nucleic acids are completely sequestered. The liposome may contain one or more nucleic acids and is administered to a mammalian host to efficiently deliver its contents to a target cell. The liposomes in the present invention comprise DOTAP and cholesterol or a cholesterol derivative. In certain embodiments, the ratio of DOTAP to cholesterol, cholesterol derivative or cholesterol mixture is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to 1:3, more preferably 2:1 to 1:2, and most preferably 1:1. In further preferred embodiments, the DOTAP and/or cholesterol concentrations are about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, or 30 mM. The DOTAP and/or Cholesterol concentration can be between about 1 mM to about 20 mM, 1 mM to about 18 mM, 1 mM to about 16 mM, about 1 mM to about 14 mM, about 1 mM to about 12 mM, about 1 mM to about 10 mM, 1 to 8 mM, more preferably 2 to 7 mM, still more preferably 3 to 6 mM and most preferably 4 to 5 mM. Cholesterol derivatives may be readily substituted for the cholesterol or mixed with the cholesterol in the present invention. Many cholesterol derivatives are known to the skilled artisan. Examples include but are not limited to cholesterol acetate and cholesterol oleate. A cholesterol mixture refers to a composition that contains at least one cholesterol or cholesterol derivative.

The formulation may also be extruded using a membrane or filter, and this may be performed multiple times. Such techniques are well-known to those of skill in the art, for example in Martin (1990). Extrusion may be performed to homogenize the formulation or limit its size.

Formulations of the present invention are extremely stable and can complex nucleic acids over a wide range of nucleic acid:liposome ratios. This "range" allows optimization of the complexes for delivery in vivo. The stability of DOTAP: Cholesterol liposomes at high concentrations of liposome and DNA allows further for increased concentrations of DNA for delivery and expression.

A contemplated method for preparing liposomes in certain embodiments is heating, sonicating, and sequential extrusion of the lipids through filters of decreasing pore size, thereby resulting in the formation of small, stable liposome structures. This preparation produces liposomal complexesor liposomes only of appropriate and uniform size, which are structurally stable and produce maximal activity.

For example, it is contemplated in certain embodiments of the present invention that DOTAP:Cholesterol liposomes are prepared by the methods of Templeton et al. (1997; incorporated herein by reference). Thus, in one embodiment, DOTAP (cationic lipid) is mixed with cholesterol (neutral lipid) at equimolar concentrations. This mixture of powdered lipids is then dissolved with chloroform, the solution dried to a thin film and the film hydrated in water containing 5% dextrose (w/v) to give a final concentration of 20 mM DOTAP and 20 mM cholesterol. The hydrated lipid film is rotated in a 50° C. water bath for 45 minutes, then at 35° C. for an additional 10 minutes and left standing at room temperature overnight. The following day the mixture is sonicated for 5 minutes at 50° C. The sonicated mixture is transferred to a tube and heated for 10 minutes at 50° C. This mixture is sequentially extruded through syringe filters of decreasing pore size (1 µm, 0.45 µm, 0.2 µm, 0.1 µm).

It also is contemplated that other liposome formulations and methods of preparation may be combined to impart desired DOTAP:Cholesterol liposome characteristics. Alternate methods of preparing lipid-based formulations for nucleic acid delivery are described by Saravolac et al. (WO 99/18933). Detailed are methods in which lipids compositions are formulated specifically to encapsulate nucleic acids. In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

2. Liposome-Mediated Nucleic Acid Delivery

In certain embodiments, anti-hyperproliferative genes are delivered in vivo via liposomes to treat hyperproliferative diseases. The liposome-mediated nucleic acid delivery and expression of foreign DNA in vitro has been successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In one example of the present invention, the liposome complex (DNA:lipid complex or DNA lipoplex) is prepared by diluting a given nucleic acid and lipids in 5% dextrose in water to obtain an appropriate concentration of nucleic acid and lipids. Equal volumes of nucleic acid and lipids, at a concentration to obtain about 25 µg, 50 µg, 75 µg, 100 µg, 110 µg, 120 µg, 125 µg, 130 µg, 140 µg, 150 µg, 160 µg, 170 µg, 180 µg, 190 µg, 200 µg, 210 µg, 220 µg, 225 µg, 230 µg, 240 µg, 250 µg, 260 µg, 270 µg, 275 µg, 280 µg, 290 µg, 300 µg, 310 µg, 320 µg, 325 µg, 330 µg, 340 µg, 350 µg, 360 µg, 370 µg, 375 µg, 400 µg, 425 µs, 450 µg, 500 µg, 550 µg, 600 µg, 650 µg, 700 µg, 750 µg, 800 µg, 850 µg, 900 µg, 950 µg, or 1000 µg of nucleic acid per 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 22 mM, 24 mM, 26 mM, 28 mM, 30 mM, 32 mM, 34 mM, 36 mM, 38 mM, or 40 mM lipids per 50, 100, 150, 200, 300, 400, 500, 600, 700, 800, 900, 1000, 1100, 1200, 1300, 1400, 1500, 2000, 2500, 3000, 3500, 4000, 4500, 5000, 5500, 6000, 7000, 8000, 9000, or 10,000 µl, as well as 15, 20, 25, or 50 ml is mixed by adding the nucleic acid rapidly to the surface of the lipid solution followed by two rapid up and down expulsions to effect rapid mixing.

Various nucleic acids may be added to these liposomes in a wide range of concentrations. Nucleic acids are preferably added to the liposomes at a concentration of 20, 25, 50, 75, 100, 110, 120, 130, 140, 150, 160, 170, 180, 190, 200, 225, 275, 300, 350, 375, 400, 450, 500, 550, 600, 650, 700, 750, 800, 850, 900, 950, or 1000 µg per 50, 100, 150, 200, 300, 400, 500, 600, 700, 800, 900, 1000, 1100, 1200, 1300, 1400, 1500, 2000, 2500, 3000, 3500, 4000, 4500, 5000, 5500, 6000, 7000, 8000, 9000, or 10,000 µl, as well as 15, 20, 25, 50 ml final volume. These concentrations vary widely depending upon the ratio of DOTAP to cholesterol, cholesterol derivative or cholesterol mixture in the particular liposome preparation. The actual dosage amount of liposome-nucleic acid administered to a patient can be determined by physical and physiological factors such as body weight, severity of condition, idiopathy of the patient and on the route of administration. With these considerations in mind, the dosage of liposome-nucleic acid complex for a particular subject and/or course of treatment can readily be determined.

As described in other sections, the liposomes of the present invention containing nucleic acid can be administered intravenously, intradermally, intra-arterially, intraperitoneally, intralesionally, intracranially, intra-articularly, intraprostaticaly, intrapleurally, intratracheally, intranasally, intravitreally, intravaginaly, rectally, topically, intratumorally, intramuscularly, intraperitoneally, subcutaneously, intravesicularlly, mucosally, intrapericardially, orally and/or using aerosol, injection, infusion, continuous infusion, localized perfusion bathing target cells directly or via a catheter and/or lavage.

3. Targeting Moieties for Liposome Delivery

The present invention provides also a targeting means, such that the liposomes can be delivered to specific cell types. Because the nucleic acid is sequestered in the liposome's cavity, targeted delivery is achieved by the addition of ligands without compromising the ability of these liposomes to bind and deliver large amounts of the nucleic acid. It is contemplated that this will enable delivery to specific organs and tissues. The targeting specificity of the ligand-based delivery systems are based on the distribution of the ligand receptors on different cell types. The targeting ligand may either be non-covalently or covalently associated with the lipid complex.

Targeting ligands are any ligand specific for a characteristic component of the targeted region. Preferred targeting ligands include proteins such as polyclonal or monoclonal antibodies, antibody fragments, or chimeric antibodies, enzymes, or hormones, or sugars such as mono-, oligo- and poly-saccharides. In certain embodiments of the invention, contemplated targeting ligands interact with integrins, proteoglycans, glycoproteins, receptors or transporters. Suitable ligands include any that are specific for cells of the target organ, or for structures of the target organ exposed to the circulation as a result of local pathology, such as tumors.

In certain embodiments of the present invention, in order to enhance the transduction of resistant cells, to increase transduction of target cells, or to limit transduction of undesired cells, antibody or cyclic peptide targeting moieties (ligands) are associated with the lipid complex. The antibody targeting moiety in particular examples is a monoclonal anti-EGF receptor antibody. EGF stimulates cell growth and proliferation through interaction with an EGF receptor. EGF receptors are distributed on the cell surface of various organs and are present in burns, wounds, dermis and tumors. In particular embodiments, the peptide targeting moiety is a cyclic peptide containing within its sequence a RGD integrin binding motif. Ligands such as the RGD peptide that bind to integrins on the cell surface can mediate internalization, thus increasing the efficiency of delivery of the targeted complex. The targeting peptide may include an RGDFV sequence, wherein the peptide includes the RGD sequence in which the peptide is from 3 to 30 amino acids in length. In other embodiments the RGD integrin binding motif is from 3 to 20 amino acids in length or 4 to 10 amino acids in length. In particular embodiments of the present invention, the RGD integrin binding motif is a peptide of 5 amino acids in length. Although cyclic peptides which contain the RGD integrin binding motif within its sequence are preferred, linear peptides may also be utilized in the present invention. Ligands may be identified by panning phage display libraries against cells and/or tissues of interest.

Contemplated also in the present invention is a targeting moiety comprising an EGF receptor binding peptide ligand (e.g., EGF or an EGF fragment).

Liposomes have been described further that specifically target cells of the mammalian central nervous system (U.S. Pat. No. 5,786,214, specifically incorporated herein by reference in its entirety). The liposomes are composed essentially of N-glutarylphosphatidylethanolamine, cholesterol and oleic acid, wherein a monoclonal antibody specific for neuroglia is conjugated to the liposomes.

The present invention further contemplates that the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

Antibodies described by Nicholson et al. (U.S. Pat. No. 5,902,584), which bind the G-CSF extracellular domain can be used in the present invention for targeting liposomes. Alternatively, monoclonal antibody fragments may be used to target delivery to specific organs in the animal including brain, heart, lungs or liver. An exemplary method for targeting viral particles to cells that lack a single cell-specific marker is described (U.S. Pat. No. 5,849,718). For example, antibody A may have specificity for tumor, but also for normal heart and lung tissue, while antibody B has specificity for tumor but also normal liver cells. Clearly, the use of antibody A or antibody B alone to deliver an anti-proliferative nucleic acid to the tumor would possibly result in unwanted damage to heart and lung or liver cells. However, antibody A and antibody B can be used together for improved cell targeting. Thus, antibody A is coupled to a gene encoding an anti-proliferative nucleic acid and is delivered, via a receptor mediated uptake system, to tumor as well as heart and lung tissue. However, the gene is not transcribed in these cells as they lack a necessary transcription factor. Antibody B is coupled to a universally active gene encoding the transcription factor necessary for the transcription of the anti-proliferative nucleic acid and is delivered to tumor and liver cells. Therefore, in heart and lung cells only the inactive anti-proliferative nucleic acid is delivered, where it is not transcribed, leading to no adverse effects. In liver cells, the gene encoding the transcription factor is delivered and transcribed, but has no effect because no an anti-proliferative nucleic acid gene is present. In tumor cells, however, both genes are delivered and the transcription factor can activate transcription of the anti-proliferative nucleic acid, leading to tumor-specific toxic effects.

Many other ligands may be employed for this targeting step of liposome preparation, depending upon the site targeted for liposome delivery. In certain embodiments, it is contemplated that liposomes are targeted to specific cell types by receptor-mediated endocytosis. For example, lactosyl ceramide, and peptides that target the LDL receptor related proteins, such as apolipoprotein E3 ("Apo E") have been useful in targeting liposomes to the liver (Spanjer and Scherphof, 1983; WO 98/0748). The asialoglycoprotein, asialofetuin, which contains terminal galactosyl residues, also has been demonstrated to target liposomes to the liver (Spanjer and Scherphof, 1983; Hara et al., 1996). The sugars mannosyl, fucosyl or N-acetyl glucosamine, when coupled to the backbone of a polypeptide, bind the high affinity manose receptor (U.S. Pat. No. 5,432,260, specifically incorporated herein by reference in its entirety). Thus, these glycoproteins can be conjugated to liposomes of the present invention and are contemplated as useful for targeting specific cells (e.g., macrophages).

Folate and the folate receptor have also been described as useful for cellular targeting (U.S. Pat. No. 5,871,727). In this example, the vitamin folate is coupled to the complex. The folate receptor has high affinity for its ligand and is over-expressed on the surface of several malignant cell lines, including lung, breast and brain tumors. Anti-folate such as methotrexate may also be used as targeting ligands. Transferrin mediated delivery systems target a wide range of replicating cells that express the transferrin receptor (Gilliland et al., 1980).

The addition of targeting ligands for gene delivery for the treatment of hyperproliferative diseases permits the delivery of genes whose gene products are more toxic than do non-targeted systems. Examples of the more toxic genes that can be delivered includes pro-apoptotic genes such as Bax and Bak plus genes derived from viruses and other pathogens such as the adenoviral E4orf4 and the *E. coli* purine nucleoside phosphorylase, a so-called "suicide gene" which converts the prodrug 6-methylpurine deoxyriboside to toxic purine 6-methylpurine. Other examples of suicide genes used with prodrug therapy are the *E. coli* cytosine deaminase gene and the HSV thymidine kinase gene.

It is also possible to utilize untargeted or targeted lipid complexes to generate recombinant or modified viruses in vivo. For example, two or more plasmids could be used to introduce retroviral sequences plus a therapeutic gene into a hyperproliferative cell. Retroviral proteins provided in trans from one of the plasmids would permit packaging of the second, therapeutic gene-carrying plasmid. Transduced cells, therefore, would become a site for production of non-replicative retroviruses carrying the therapeutic gene. These retroviruses would then be capable of infecting nearby cells. The promoter for the therapeutic gene may or may not be inducible or tissue specific.

Similarly, the transferred nucleic acid may represent the DNA for a replication competent or conditionally replicating viral genome, such as an adenoviral genome that lacks all or part of the adenoviral E1a or E2b region or that has one or more tissue-specific or inducible promoters driving transcription from the E1a and/or E1b regions. This replicating or conditional replicating nucleic acid may or may not contain an additional therapeutic gene such as a tumor suppressor gene or anti-oncogene.

5. Liposome-Ligand Conjugation

The liposomes of the invention can be targeted to specific regions of the body by attachment of specific targeting ligands to provide rapid accumulation and concentration of liposomes and, correspondingly, of nucleic acid molecules, in a designated tissue. The ligands contemplated for use in the present invention can be conjugated to the liposomes by a variety of methods.

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. No. 5,603,872 and U.S. Pat. No. 5,401,511, each specifically incorporated herein by reference in its entirety). Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites will be dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides and sugars. Table 2 details certain hetero-bifunctional cross-linkers considered useful in the present invention.

TABLE 2

HETERO-BIFUNCTIONAL CROSS-LINKERS

| linker | Reactive Toward | Advantages and Applications | Spacer Arm Length\after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/ Sulfo-NHS | Primary amines Carboxyl groups | Hapten-Carrier conjugation | 0 |
| ABH | Carbohydrates Nonselective | Reacts with sugar groups | 11.9 A |

In instances where a particular polypeptide does not contain a residue amenable for a given cross-linking reagent in its native sequence, conservative genetic or synthetic amino acid changes in the primary sequence can be utilized.

The targeting ligand can be either anchored in the hydrophobic portion of the complex or attached to reactive terminal groups of the hydrophilic portion of the complex. The targeting ligand can be attached to the liposome via a linkage to a reactive group, e.g., on the distal end of the hydrophilic polymer. Preferred reactive groups include amino groups, carboxylic groups, hydrazide groups, and thiol groups. The coupling of the targeting ligand to the hydrophilic polymer can be performed by standard methods of organic chemistry that are known to those skilled in the art. The total concentration of the targeting ligand can be from 0.01 to 10% mol.

6. Vectors and Regulatory Signals

Vectors of the present invention are designed, primarily, to transform hyperproliferative cells with a therapeutic gene under the control of regulated eukaryotic promoters (i.e., inducible, repressible, tissue-specific) or to transform nearby cells, such as tumor vasculature. Also, the vectors usually will contain a selectable marker if, for no other reason, to facilitate their production in vitro. However, selectable markers may play an important role in producing recombinant cells and thus a discussion of promoters is useful here.

Table 3 and Table 4 below, list inducible promoter elements and enhancer elements, respectively.

7. Eukaryotic and Viral Promoters and Enhancers Preferred for use in the present invention is the cytomegalovirus (CMV) promoter. This promoter is commercially available from Invitrogen in the vectors pcDNAIII and pVAX1, which are preferred for use in the present invention. Also contemplated as useful in the present invention are the dectin-1 and dectin-2 promoters. Below are a list of additional viral promoters, cellular promoters/enhancers and inducible promoters/enhancers that could be used in combination with the present invention. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

Another signal that may prove useful is a polyadenylation signal (e.g., hGH, BGH, SV40).

The use of internal ribosome binding sites (IRES) elements are used to create multigene, or polycistronic, messages. IRES elements are able to bypass the ribosome scanning model of 5'-methylated cap-dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

TABLE 3

Inducible Elements

| Element | Inducer | References |
|---|---|---|
| MT II | Phorbol Ester (TFA) Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Fonta et al., 1985; Sakai et al., 1986 |
| β-Interferon | poly(rI)X poly(rc) | Tavernier et al., 1983 |
| Adenovirus 5 E2 | E1a | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |

TABLE 3-continued

Inducible Elements

| Element | Inducer | References |
|---|---|---|
| HSP70 | E1a, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone α Gene | Thyroid Hormone | Chatterjee et al., 1989 |

TABLE 4

Other Promoter/Enhancer Elements

| Promoter/Enhancer | References |
|---|---|
| Immunoglobulin Heavy Chain | Hanerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| α-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $a_{1-Antitrypain}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |

TABLE 4-continued

Other Promoter/Enhancer Elements

| Promoter/Enhancer | References |
| --- | --- |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et at, 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988 |
| Human Immunodeficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator proteins.

At least one module in each promoter functions to position the start site for RNA synthesis. The best known example is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either cooperatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities.

Promoters and enhancers have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

In any event, it will be understood that promoters are DNA elements which when positioned functionally upstream of a gene leads to the expression of that gene. Most transgene constructs of the present invention are functionally positioned downstream of a promoter element.

The nucleic acids of this invention may also contain one or more introns. The inclusion of an intron has been found in many cases to lead to increased levels of transgene expression. Introns may also be included that contain binding sites for transcription factors. The nucleic acid may include a leader sequence to enhance translation such as the tripartite leader sequence of adenovirus.

The nucleic acids of this invention may be linear, branched, or circular. A preferred embodiment of the present invention utilizes plasmids that carry a eukaryotic expression cassette as well as prokaryotic sequences that allow replication in prokaryotic production systems. These plasmids may be non-replicating in a mammalian host, conditionally replicating, or replicating. An example of replicating plasmids would be those that contain an origin of replication and EBNA1 gene from the Epstein Barr virus. An example of a conditionally replicating plasmid would be one in which the EBNA-1 gene was under the control of a cell-specific, tumor-specific, or inducible promoter.

8. Antisense Molecules and Ribozymes a. Antisense

Antisense methodology takes advantage of the fact that nucleic acids tend to pair with "complementary" sequences. By complementary, it is meant that polynucleotides are those capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. An antisense polynucleotide, when introduced into a target cell, specifically bind to their target polynucleotide and interfere with transcription, RNA processing, transport, translation and/or stability. Antisense RNA constructs or molecules, or DNA encoding such antisense RNAs, may be employed to inhibit gene transcription or translation or both within a host cell, either in vitro or in vivo, such as within a host animal, including a human subject. The antisense molecule, or the DNA encoding the antisense molecule is said to be "directed against" a nucleic acid or gene whose transcription or translation is targeted. That nucleic acid or gene may encode a particular type of polypeptide, such as a growth-promoting protein, which means the antisense molecule is intended to prevent the expression of a protein that promotes growth, for example a growth factor.

Antisense constructs may be designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50-200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

B. Ribozymes

The use of specific ribozymes is claimed in the present application. The following information is provided in order to complement the earlier section and to assist those of skill in the art in this endeavor. Thus, ribozymes may also be directed against a particular nucleic acid, as were the antisense molecules discussed above.

Ribozymes are RNA-protein complexes that cleave nucleic acids in a site-specific fashion. Ribozymes have specific catalytic domains that possess endonuclease activity (Kim and Cech, 1987; Gerlack et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Several different ribozyme motifs have been described with RNA cleavage activity (reviewed in Symons, 1992). Examples that would be expected to function equivalently for the down regulation of IGFBP-2 include sequences from the Group I self splicing introns including tobacco ringspot virus (Prody et al., 1986), avocado sunblotch viroid (Palukaitis et al., 1979 and Symons, 1981), and Lucerne transient streak virus (Forster and Symons, 1987). Sequences from these and related viruses are referred to as hammerhead ribozymes based on a predicted folded secondary structure.

Other suitable ribozymes include sequences from RNase P with RNA cleavage activity (Yuan et al., 1992; Yuan and Altman, 1994), hairpin ribozyme structures (Berzal-Herranz et al., 1992; Chowrira et al., 1993) and hepatitis δ virus based ribozymes (Perrotta and Been, 1992). The general design and optimization of ribozyme directed RNA cleavage activity has been discussed in detail (Haseloff and Gerlach, 1988, Symons, 1992, Chowrira, et al., 1994, and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A, C or U; Perriman, et al., 1992; Thompson, et al., 1995). The frequency of this dinucleotide occurring in any given RNA is statistically 3 out of 16. Therefore, for a given target messenger RNA of 1000 bases, 187 dinucleotide cleavage sites are statistically possible. The message for IGFBP-2 targeted here are greater than 1400 bases long, with greater than 260 possible cleavage sites.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in targeted ribozymes is simply a matter of preparing and testing a given sequence, and is a routinely practiced "screening" method known to those of skill in the art.

9. Single-Chain Antibodies, Decoys and Dominant Negatives

Another embodiment of the present invention contemplates the use a nucleic acid encoding a single-chain antibody, a decoy or a dominant negative directed at particular type of polypeptide in cells, in particular hyperproliferative cells, to block that polypeptide's activity. Single-chain antibodies, decoys, and dominant negatives can be synthesized by a cell, targeted to particular cellular compartments, and used to interfere in a highly specific manner with cell growth and metabolism (Richardson and Marasco, 1995).

Recently, single-chain antibodies were utilized for the phenotypic knockout of growth-factor receptors, the functional inactivation of p21 ras, and the inhibition of HIV-1 replication. Intracellular antibodies offer a simple and effective alternative to other forms of gene inactivation, as well as demonstrate a clear potential as reagents for cancer therapy and for the control of infectious diseases. Single-chain antigen-binding proteins also represent potentially unique molecules for targeted delivery of drugs, toxins, or radionuclides to a tumor site, and show increased accessibility to tumor cells in vivo (Yokoda et al., 1992). Single-chain antibodies that bind a growth-promoting protein can be introduced into a cell to functionally inactivate the protein.

Methods for the production of single-chain antibodies are well known to those of skill in the art. The skilled artisan is referred to U.S. Pat. No. 5,359,046, (incorporated herein by reference) for such methods. A single-chain antibody is created by fusing together the variable domains of the heavy and light chains using a short peptide linker, thereby reconstituting an antigen binding site on a single molecule.

Single-chain antibody variable fragments (scFvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Decoys and dominant negatives are polypeptides that prevent a particular polypeptide from effecting its activity. Typically, they bind the targeted polypeptide or the polypeptide against which they are directed. A decoy is all or part of a polypeptide that lures the targeted polypeptide away, to prevent the targeted polypeptide from interacting with other polypeptides with which it normally interacts. Binding of the decoy and the targeted polypeptide may sequester the targeted polypeptide such that it can no longer reach a particular part of the cell.

A dominant negative is all or part of a polypeptide that exerts a dominant effect on the targeted polypeptide and prevents it from functioning properly. For example, if the targeted polypeptide functions as a dimer (hetero- or homo-), a dominant negative could comprise the dimerization domain of another polypeptide that interacts with the targeted polypeptide but otherwise lack the remaining functional domains of the other polypeptide, such as the transducing domain. The dominant negative (dimerization domain) would bind to the targeted polypeptide, but the complex would be unable to form an active complex since other functional domains are absent. Many growth factor receptors and signal transducers, such as KIT, PDGF, FGF, and FMS, require dimerization to be able to respond to growth factors, and many transcription factors, such as JUN, FOS, and MYC, are functional only as dimers to bind DNA. Binding may also prevent the targeted polypeptide from selectively interacting with another polypeptide with which it usually interacts.

It is also contemplated by the present invention that therapies involving single-chain antibodies, decoys, and dominant negatives can be combined with other anti-cancer therapies, such as chemotherapy, radiotherapy, surgery, immunotherapy, or hormone therapy. The discussion of combined therapy with traditional anti-cancer therapies employed herein is incorporated into this section by reference.

C. Pharmaceutical Formulations and Nucleic Acid Delivery

In a preferred embodiment of the present invention, a formulation of a pharmaceutically acceptable lipid for the delivery of therapeutic nucleic acids for the treatment of hyperproliferative diseases is contemplated. Hyperproliferative diseases that are most likely to be treated in the present invention are those that result from mutations in an oncogene and/or the reduced expression of a wild type protein in the hyperproliferative cells. Examples of hyperproliferative diseases contemplated for treatment are lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, head and neck, cervix, intestine, pancrease and other organs; as well as colorectal cancer, breast cancer, bladder cancer, and any other hyperproliferative diseases that may be treated by administering a nucleic acid encoding a protein with anti-proliferative properties. Examples of other hyperproliferative conditions include but are not limited to adenomas, benign prostatic hypertrophy, intraepithelial neoplasia, endometriosis, and colonic polyps.

In certain embodiments, the present invention also concerns formulations of one or more nucleic acid compositions for administration to a mammal. For the treatment of hyperproliferative disease in humans, it is contemplated that a pharmaceutical lipid formulation, comprising DOTAP and cholesterol, a cholesterol derivative or a cholesterol mixture, and a nucleic acid under the control of a promoter operable in eukaryotic cells (e.g., CMV IE, dectin-1, dectin-2) will be used. It will also be understood that, if desired, the lipid: nucleic acid compositions disclosed herein may be administered in combination with other agents as well, e.g., various pharmaceutically-active agents. As long as the composition comprises at least one nucleic acid, there is virtually no limit to other components which may also be included, given that the additional agents do not cause a significant adverse effect to the organism upon administration.

The formulation of pharmaceutically-acceptable excipients and carrier solutions are well-known to those of skill in the art, as is the development of suitable dosing and treatment regimens for using the particular compositions described herein in a variety of treatment regimens, including, e.g., intradermal, parenteral, intravenous, intramuscular, intranasal, intrapericardial, mucosal, topical, aerosol and oral administration and formulation.

D. Injectable Compositions and Delivery

To kill cells, inhibit cell growth, inhibit metastasis, decrease tumor or tissue size and otherwise reverse or reduce the malignant phenotype of tumor cells, using the methods and compositions of the present invention, one would generally contact a hyperproliferative cell with the therapeutic expression construct. The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation. The formulations of the invention may be administered 1, 2, 3, 4, 5, 6, 7, 8, 9, 10, 11, 12, 13, 14, 15, 16, 17, 18, 19, 20, 21, 22, 23, 24, 25, or more times. They may also be administered 1, 2, 3, 4, 5, 6, 7, 8 or more times a day, or they maybe administered every 1, 2, 3, 4, 5, 6, or 7 days, or every 1, 2, 3, 4, or 5 weeks, or every 1, 2, 3, 4, 5, 6, 7, 8, 9, 10, 11, or 12 months.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (preferably 10 ml), while for tumors of <4 cm, a volume of about 1-3 ml will be used (preferably 3 ml). Multiple injections delivered as single dose comprise about 0.1 to about 0.5 ml volumes. The liposome:nucleic acid may advantageously be contacted by administering multiple injections to the tumor, spaced at approximately 1 cm intervals.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a DOTAP:Cholesterol formulation comprising a nucleic acid construct encoding an anti-proliferative protein. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. Treatments with therapeutic liposomal formulations may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

The preferred method of the lipid: nucleic acid expression construct delivery to hyperproliferative cells in the present invention is via intravenous injection. However, the pharmaceutical compositions disclosed herein may alternatively be administered parenterally, intradermally, intramuscularly, or even intraperitoneally as described in U.S. Pat. No. 5,543,158; U.S. Pat. No. 5,641,515 and U.S. Pat. No. 5,399,363 (each specifically incorporated herein by reference in its entirety). Injection of nucleic acid constructs may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions or liposomal suspension, particularly multi-vial formulations, of the active compounds as free base or pharmacologically acceptable salts may be prepared in water, in buffered solutions, and suitably mixed with a surfactant, such as hydroxypropylcellulose. Dispersions may also be prepared in glycerol, liquid polyethylene glycols, and mixtures thereof and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. For multi-viral formulations the carrier compounds, the liposome, prepared in sterile suspensions that are suitable for deliver to humans.

For single viral formulations, suspensions of the active compounds in the liposome carrier with and without additional components may be used as described in the instant application.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds and carriers in the required amount in the appropriate solvent with various of the other ingredients enumerated above, as required, prepared by aseptic procedure and/or followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of associated protein(s)) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

E. Additional Modes of Delivery

In addition to the methods of delivery described above, the following techniques are also contemplated as alternative methods of therapeutic nucleic acid delivery. Sonophoresis (i.e., ultrasound) has been used and described in U.S. Pat. No. 5,656,016 (specifically incorporated herein by reference in its entirety) as a device for enhancing the rate and efficacy of drug permeation into and through the circulatory system. Similarly, electroporation has been used to deliver genes in vivo (Suzuki et al., 1998). Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. No. 5,770,219 and U.S. Pat. No. 5,783,208), rectal delivery (U.S. Pat. No. 5,811,128) and feedback controlled delivery (U.S. Pat. No. 5,697,899), each specifically incorporated herein by reference in its entirety.

F. Pharmaceuticals and Methods of Treating Cancer

In a particular aspect, the present invention provides methods for the treatment of various hyperproliferative diseases. Treatment methods will involve treating an individual with an effective amount of a lipid formulation, as described above, containing a nucleic acid of interest. An effective amount is described, generally, as that amount sufficient to detectably and repeatedly ameliorate, reduce, minimize or limit the extent of the disease or its symptoms. More rigorous definitions may apply, including elimination, eradication or cure of disease.

In order to increase the effectiveness of a liposome: nucleic acid complex it may be desirable to combine these compositions with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that anti-proliferative gene therapy could be used similarly in conjunction with chemotherapeutic, radiotherapeutic, or immunotherapeutic intervention, in addition to other pro-apoptotic or cell cycle regulating agents.

To kill cells, inhibit cell growth, inhibit metastasis, decrease tumor or tissue size and otherwise reverse or reduce the malignant phenotype of tumor cells, using the methods and compositions of the present invention, one would generally contact a hyperproliferative cell with the therapeutic expression construct. This may be combined with compositions comprising other agents effective in the treatment of hyperproliferative cells. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes a nucleic acid and the other includes the second agent.

Alternatively, the lipid complex therapy may precede or follow the other agent treatment by intervals ranging from minutes to weeks. In embodiments where the other agent and nucleic acid are applied separately to the cell, one would generally ensure that a significant period of time did not expire between the time of each delivery, such that the agent and nucleic acid would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, gene therapy is "A" and the radio- or chemotherapeutic or other therapeutic agent is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the therapeutic nucleic acid constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described lipid formulation therapy.

Aqueous compositions of the present invention comprise an effective amount of the compound, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time. Unit dose of the present invention may conveniently be described in terms of nucleic acid mass (μg) of the nucleic acid in the lipid complex. Unit doses range from 1, 25, 50, 75, 100, 125, 150, 175, 200, 225, 250, 300, 400, 500, 600, 700, 800, 900, 1000 μg and higher.

Preferably, patients will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

One of the preferred embodiments of the present invention involves the use of lipid nucleic acid complex to deliver therapeutic genes to hyperproliferative cells for the treatment of cancer. Cancer cells include cancers of the lung, brain, prostate, kidney, liver, ovary, breast, skin, stomach, esophagus, head and neck, testicles, colon, rectum, cervix, lymphatic system and blood. Of particular interest are non-small cell lung carcinomas including squamous cell carcinomas, adenocarcinomas and large cell undifferentiated carcinomas.

According to the present invention, one may treat the cancer by directly injecting a tumor with the lipid complex. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe, infusion or catherization is preferred. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

For tumors of >4 cm, the volume to be administered will be about 4-10 ml (preferably 10 ml), while for tumors of <4 cm, a volume of about 1-3 ml will be used (preferably 3 ml).

Multiple injections delivered as single dose comprise about 0.1 to about 0.5 ml volumes. The lipid complex may advantageously be contacted by administering multiple injections to the tumor, spaced at approximately 1 cm intervals.

In certain embodiments, the tumor being treated may not, at least initially, be resectable. Treatments with therapeutic lipid complex formulations may increase the resectability of the tumor due to shrinkage at the margins or by elimination of certain particularly invasive portions. Following treatments, resection may be possible. Additional lipid complex treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated. For systemic administration the liposome complexes may be administered from 0.5 to several hours by infusion with a pharmaceutically acceptable diluent such as 5% dextrose in water, Ringer's, 0.5% NaCl. The systemic administration may occur once per week for multiple weeks over the course of months.

Preferably, patients will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

1. Gene Therapy

In yet another embodiment, the secondary treatment is a secondary gene therapy in which a second therapeutic polynucleotide is administered before, after, or at the same time a first therapeutic polynucleotide. Alternatively, a single vector encoding both genes may be used. A variety of proteins are encompassed within the invention, some of which have been described earlier in the instant application.

2. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, bisulfan, A wide variety of chemotherapeutic agents may be used in combination with the use of nucleic acid molecules in a pharmaceutically acceptable lipid formulation in the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, corticosteroid hormones, mitotic inhibitors, and nitrosoureas, and any analog or derivative variant thereof. It is contemplated that the nucleic acid formulations described herein can be used in combination with one or more of these agents according to the present invention.

a. Alkylating Agents

Alkylating agents are drugs that directly interact with genomic DNA to prevent the cancer cell from proliferating. This category of chemotherapeutic drugs represents agents that affect all phases of the cell cycle, that is, they are not phase-specific. Alkylating agents can be implemented to treat chronic leukemia, non-Hodgkin's lymphoma, Hodgkin's disease, multiple myeloma, and particular cancers of the breast, lung, and ovary. They include: busulfan, chlorambucil, cisplatin, cyclophosphamide (cytoxan), dacarbazine, ifosfamide, mechlorethamine (mustargen), and melphalan. Troglitazaone can be used to treat cancer in combination with any one or more of these alkylating agents, some of which are discussed below.

i. Busulfan

Busulfan (also known as myleran) is a bifunctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

ii. Chlorambucil

Chlorambucil (also known as leukeran) is a bifunctional alkylating agent of the nitrogen mustard type that has been found active against selected human neoplastic diseases. Chlorambucil is known chemically as 4-[bis(2-chloroethyl) amino] benzenebutanoic acid.

Chlorambucil is available in tablet form for oral administration. It is rapidly and completely absorbed from the gastrointestinal tract. After single oral doses of 0.6-1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remington's Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

iii. Cisplatin

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15-20 mg/m$^2$ for 5 days every three weeks for a total of three courses. Exemplary doses may be 0.50 mg/m$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/m$^2$, 10 mg//m$^2$. Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

iv. Cyclophosphamide

Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [(ClCH$_2$CH$_2$)$_2$N—POCl$_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

v. Melphalan

Melphalan, also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis(2-chloroethyl)amino]-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKa$_1$ of ~2.1. Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject b. Antimetabolites Antimetabolites disrupt DNA and RNA synthesis. Unlike alkylating agents, they specifically influence the cell cycle during S phase. They have used to combat chronic leukemias in addition to tumors of breast, ovary and the gastrointestinal tract. Antimetabolites include 5-fluorouracil (5-FU), cytarabine (Ara-C), fludarabine, gemcitabine, and methotrexate.

i. 5-Fluorouracil

5-Fluorouracil (5-FU) has the chemical name of 5-fluoro-2,4(1H,3H)-pyrimidinedione. Its mechanism of action is thought to be by blocking the methylation reaction of deoxyuridylic acid to thymidylic acid. Thus, 5-FU interferes with the syntheisis of deoxyribonucleic acid (DNA) and to a lesser extent inhibits the formation of ribonucleic acid (RNA). Since DNA and RNA are essential for cell division and proliferation, it is thought that the effect of 5-FU is to create a thymidine deficiency leading to cell death. Thus, the effect of 5-FU is found in cells that rapidly divide, a characteristic of metastatic cancers.

c. Antitumor Antibiotics

Antitumor antibiotics have both antimicrobial and cytotoxic activity. These drugs also interfere with DNA by chemically inhibiting enzymes and mitosis or altering cellular membranes. These agents are not phase specific so they work in all phases of the cell cycle. Thus, they are widely used for a variety of cancers. Examples of antitumor antibiotics include bleomycin, dactinomycin, daunorubicin, doxorubicin (Adriamycin), and idarubicin, some of which are discussed in more detail below. Widely used in clinical setting for the treatment of neoplasms these compounds are administered through bolus injections intravenously at doses ranging from 25-75 mg/m$^2$ at 21 day intervals for adriamycin, to 35-100 mg/m$^2$ for etoposide intravenously or orally.

i. Doxorubicin

Doxorubicin hydrochloride, 5,12-Naphthacenedione, (8s-cis)-10-[(3-amino-2,3,6-trideoxy-a-L-lyxo-hexopyranosyl)oxy]-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

ii. Daunorubicin

Daunorubicin hydrochloride, 5,12-Naphthacenedione, (8S-cis)-8-acetyl-10-[(3-amino-2,3,6-trideoxy-a-L-lyxo-hexanopyranosyl)oxy]-7,8,9,10-tetrahydro-6,8,11-trihydroxy-10-methoxy-, hydrochloride; also termed cerubidine and available from Wyeth. Daunorubicin intercalates into DNA, blocks DAN-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m$^2$ for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

iii. Mitomycin

Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg. bolus injection is 17 minutes. After injection of 30 mg, 20 mg, or 10 mg I.V., the maximal serum concentrations were 2.4 mg/mL, 1.7 mg/mL, and 0.52 mg/mL, respectively. Clearance is effected primarily by metabolism in the liver, but metabolism occurs in other tissues as well. The rate of clearance is inversely proportional to the maximal serum concentration because, it is thought, of saturation of the degradative pathways. Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

iv. Actinomycin D

Actinomycin D (Dactinomycin) [50-76-0]; $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors that fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

v. Bleomycin

Bleomycin is a mixture of cytotoxic glycopeptide antibiotics isolated from a strain of *Streptomyces verticillus*. Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 mL per minute, the serum or plasma terminal elimination half-life of bleomycin is approximately 115 minutes. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin. Bleomycin may be given by the intramuscular, intravenous, or subcutaneous routes. It is freely soluble in water.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

d. Corticosteroid Hormones

Corticosteroid hormones are useful in treating some types of cancer (lymphoma, leukemias, and multiple myeloma). Though these hormones have been used in the treatment of many non-cancer conditions, they are considered chemotherapy drugs when they are implemented to kill or slow the growth of cancer cells. Corticosteroid hormones can increase the effectiveness of other chemotherapy agents, and consequently, they are frequently used in combination treatments. Prednisone and dexamethasone are examples of corticosteroid hormones.

e. Mitotic Inhibitors

Mitotic inhibitors include plant alkaloids and other natural agents that can inhibit either protein synthesis required for cell division or mitosis. They operate during a specific phase during the cell cycle. Mitotic inhibitors comprise docetaxel, etoposide (VP16), paclitaxel, taxol, vinblastine, vincristine, and vinorelbine.

i. Etoposide (VP16)

VP16 is also known as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m$^2$ or as little as 2 mg/m$^2$, routinely 35 mg/m$^2$, daily for 4 days, to 50 mg/m$^2$, daily for 5 days have also been used. When given orally, the dose should be doubled. Hence the doses for small cell lung carcinoma may be as high as 200-250 mg/m$^2$. The intravenous dose for testicular cancer (in combination therapy) is 50 to 100 mg/m$^2$ daily for 5 days, or 100 mg/m$^2$ on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

ii. Taxol

Taxol is an experimental antimitotic agent, isolated from the bark of the ash tree, *Taxus brevifolia*. It binds to tubulin (at a site distinct from that used by the *vinca* alkaloids) and promotes the assembly of microtubules. Taxol is currently being evaluated clinically; it has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

iii. Vinblastine

Vinblastine is another example of a plant aklyloid that can be used in combination with gene therapy for the treatment of cancer and precancer. When cells are incubated with vinblastine, dissolution of the microtubules occurs.

Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours. Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

iv. Vincristine

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes. Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m$^2$, 0.05 mg/m$^2$, 0.06 mg/m$^2$, 0.07 mg/m$^2$, 0.08 mg/m$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

f. Nitrosureas

Nitrosureas, like alkylating agents, inhibit DNA repair proteins. They are used to treat non-Hodgkin's lymphomas, multiple myeloma, malignant melanoma, in addition to brain tumors. Examples include carmustine and lomustine.

a. Carmustine

Carmustine (sterile carmustine) is one of the nitrosoureas used in the treatment of certain neoplastic diseases. It is 1,3bis (2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

Sterile carmustine is commonly available in 100 mg single dose vials of lyophilized material. The recommended dose of carmustine as a single agent in previously untreated patients is 150 to 200 mg/m$^2$ intravenously every 6 weeks. This may be given as a single dose or divided into daily injections such as 75 to 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m$^2$, 20 mg/m$^2$, 30 mg/m$^2$ 40 mg/m$^2$ 50 mg/m$^2$ 60 mg/m$^2$ 70 mg/m$^2$ 80 mg/m$^2$ 90 mg/m$^2$ 100 mg/m$^2$. The skilled artisan is directed to, "Remington's Pharmaceutical Sciences" 15th Edition, chapter 61. Some variation in dosage will necessarily occur depending on the condition of the ii. Lomustine Lomustine is one of the nitrosoureas used in the treatment of certain neoplastic diseases. It is 1-(2-chloro-ethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m² to 100 mg/m², about half of the radioactivity given was excreted in the form of degradation products within 24 hours. The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/m² as a single oral dose every 6 weeks. In individuals with compromised bone marrow function, the dose should be reduced to 100 mg/m² every 6 weeks. When lomustine is used in combination with other myelosuppressive drugs, the doses should be adjusted accordingly. It is understood that other doses may be used for example, 20 mg/m² 30 mg/m², 40 mg/m², 50 mg/m², 60 mg/m², 70 mg/m², 80 mg/m², 90 mg/m², 100 mg/m², 120 mg/m² or any doses between these figures as determined by the clinician to be necessary for the individual being treated.

g. Miscellaneous Agents

Some chemotherapy agents do not qualify into the previous categories based on their activities. However, it is contemplated that they are included within the method of the present invention for use in combination therapies of cancer with gene therapy involving lipid formulations. They include amsacrine, L-asparaginase, tretinoin, and Tumor Necrosis Factor (TNF), some of which are discussed below.

i. Tumor Necrosis Factor

Tumor Necrosis Factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

3. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

4. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. Mda-7 gene transfer to tumor cells causes tumor cell death and apoptosis. The apoptotic tumor cells are scavenged by reticuloendothelial cells including dendritic cells and macrophages and presented to the immune system to generate anti-tumor immunity (Rovere et al., 1999; Steinman et al., 1999). The soluble form of MDA-7 protein has cytokine-like structure and activities, such as activation of immune cells. The combination of therapeutic modalities, i.e., direct cytotoxic activity and immune activation by MDA-7 would provide therapeutic benefit in the treatment of cancer.

Immunotherapy could also be used as part of a combined therapy, in conjunction with Ad-mda7 gene therapy. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine pro-apoptotic effect, mediated by Ad-mda7 treatment with immune stimulatory effects. The latter may be inherent in the soluble MDA-7 protein. However, alternate immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with Ad-mda7 will enhance anti-tumor effects (Ju et al., 2000).

a. Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

b. Active Immunotherapy

In active immunotherapy, an antigenic peptide, polypeptide or protein, or an autologous or allogenic tumor cell composition or "vaccine" is administered, generally with a distinct bacterial adjuvant (Ravindranath & Morton, 1991; Morton & Ravindranath, 1996; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anticarbohydrate antibodies.

c. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated anigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond.

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

6. Other Anti-Cancer Therapies

It is contemplated that other therapies and agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adehesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adehesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Animals.

3-6 wk-old female/male BALB/c nude and Beige/SCID mice were purchased from Harlan Inc. (Indianapolis, Ind.) and Charles River laboratories, respectively. Animals were housed in specific pathogen-free units of the Department of Veterinary Medicine and Surgery at M. D. Anderson Cancer Center.

Preparation of Lipid Formulation.

DOTAP:Cholesterol liposomes were prepared by the methods of Templeton et al. (1997). Briefly, DOTAP (cationic lipid) was mixed with cholesterol (neutral lipid) at equimolar concentrations. This mixture of powdered lipids was then dissolved with HPLC grade chloroform (Mallinckrodt) in a 1 L round bottom flask. The lipid solution was dried to a thin film at 30° C. for 30 minutes using a Buchi rotary evaporator. The flask containing the thin film was further dried under vacuum for 15 minutes. The film was hydrated in water containing 5% dextrose (w/v) to give a final concentration of 20 mM DOTAP and 20 mM cholesterol. The hydrated lipid film was rotated in a 50° C. water bath for 45 minutes and then at 35° C. for an additional 10 minutes. The mixture was left standing at room temperature overnight. The following day the mixture was sonicated for 5 minutes at 50° C. The sonicated mixture was transferred to a tube and was heated for 10 minutes at 50° C. This mixture was sequentially extruded through Whatman syringe filters of decreasing pore size (1 μm, 0.45 μm, 0.2 μm, 0.1 μm). The 0.2 μm and 0.1 μm were Whatman Anotop filters. Filtrate was stored at 4° C. under argon gas.

Lipid Complex Preparation.

Lipid complex (DNA: lipid complex) were prepared on the day of application. DNA and lipids were diluted in 5% dextrose in water to obtain an appropriate concentration of DNA and lipids. Equal volumes of DNA and lipids, at a concentration to obtain 100 μg of DNA/5 mM lipids/100 μl, were mixed by adding the DNA rapidly to the surface of the lipid solution followed by two rapid up and down expulsions from a Pipetman.

Lipid Complex Characterization.

Lipid complexes were produced as previously described and electrophoresed at 60-80 V/cm$^2$ through a 0.8% agarose gel using 1×TBE as running buffer at room temperature for 1-2 hours. DNA is visible as an ethidium bromide stained band characteristic of uncut source plasmid. DNA:lipid is not visible with this technique due to the size of the complex and its inability to enter the agarose gel. The mean particle size was determined by dynamic light scattering using a Coulter N4 particle size analyzer. The average particle size is 310-320 nm. The various DNAs did not alter the particle size of the lipid complex.

Reagents and Cell Lines.

DOTAP was purchased from Avanti Polar Lipids. Cholesterol (high purity) was purchased from Calbiochem. H1299, A549, H322, and H226Br tumor cell lines were a gift from Dr. Adi Gazdar and Dr. John Minna, University of Texas Southwestern Medical Center, Dallas, Tex.

Cell Preparation.

In vitro transfection assay. Cells were plated at a density of $5 \times 10^5$ cells per 60 mm$^2$ in RPMI/10% FBS media and grown in 5% $CO_2$ at 37° C.

Tail Vein Injections.

Cells were plated at an approximately 20-40% confluency in RPMI/10% FBS media, supplemented with penicillin, streptomycin and fungizone, and grown in 5% $CO_2$ at 37° C. until approximately 80% confluent. A549 cells were grown and maintained in Ham's F12 instead of RPMI. Cells were washed twice in PBS, trypsinized, and counted. Cells were diluted to a concentration of $1 \times 10^6$ cells/200 μl in PBS.

Subcutaneous Injections.

Cells were plated at a density of approximately 20-40% confluency in 150 mm$^2$ dishes in RPMI/10% FBS media and grown in 5% $CO_2$ at 37° C. until approximately 80% confluent. Cells were washed twice in PBS, trypsinized, and counted. Cells were diluted to a concentration of $5 \times 10^6$ cells/100 μl in PBS.

Solid Tumor Induction by Subcutaneous Injection.

BALB/c nude mice were injected subcutaneously with $5 \times 10^6$ tumor cells in 100 μl of PBS.

Lung Tumor Induction by Tail Vein Injection.

Beige SCID mice were injected via the tail vein with $1 \times 10^6$ tumor cells in 200 μl of PBS using a 27 gauge syringe needle.

Analysis of p53 Protein Expression.

Expression of p53 was detected by western blotting of transfected cells. Expression of p53 in vivo was determined by immunohistochemical staining of tumor sections.

Example 2

In Vitro Lipid Complex Gene Delivery to Tumor Cell Lines

In vitro transfection studies were used to show lipid complex gene transfer into the tumor cell lines utilized in subsequent studies. Lipid: nucleic acid complex containing an expression construct encoding green fluorescent protein (GFP, lipid complex-GFP) was used as a reporter construct. Efficiencies of gene transfer were studied in the tumor cell lines H1299, H322, H226Br, and A549. Cell lines were plated as previously described and grown overnight. The following day, cells were transfected with 5 μl of lipid complex-GFP (50 μg/100 μl of lipid complex-GFP) and grown in serum free media for 3 hours at 37° C. in 5% $CO_2$.

After a 3 hour incubation, serum free media was aspirated and replaced with complete media. Cells were grown overnight at 37° C. in 5% $CO_2$. Cells were harvested on the following day and washed twice with PBS. Cells were resuspended in a final volume of 300 µl PBS. GFP fluorescence was quantitated using flow assisted cell sorting (FACS) analysis (Coulter Corporation).

Example 3

In Vivo Lipid Complex Gene Delivery

Lipid complex-β gal was administered by tail vein injection into 3-4 week old female BALB/c nude mice. Lipid complex gene transfer studies to the lung were conducted by standard histochemical and immuno-histochemical staining for βgal expression. BALB/c nude mice were injected with (1) Ad-βgal at $10^9$ pfu, (2) βgal DNA 100 µg/200 µl volume, and (3) lipid complex-βgal 100 µg/5 mM lipids in a 200 µl volume. Mice were killed 48 hours post injection and exsanguiated. Lung tissue from each experimental group was harvested and mounted in O.C.T. compound for cryosections. Tissues mounted in O.C.T. were cut into 4-6 µm thick sections. The cryosections were mounted on silane coated slides, air dried at room temperature, and stained histochemically for LacZ expression using 5-bromo-4-chloro-3-indolyl-β-D-galactopyranoside (X-Gal) substrate (Sigma) as previously described (Turner et al. 1990). After rinsing with water for 5 minutes, sections were counterstained with Meyer's hematoxylin (Sigma) or neutral red (Fisher), dehydrated in ethanol, immersed for 5 minutes in xylene, and then mounted under coverslips. Control animals not treated were included to assure specificity of the staining.

Cells positive and negative for lacZ activity were counted under a microscope at a magnification of 200× in a double blind fashion. Ad-βgal treated animals had an increase in positive cells of 4% over background. Lipid complex-βgal treated animals had an increase in positive cells of 11% over background. It can be concluded that in vivo administration of lipid complex-βgal transfects lung cells with a higher efficiency than does Ad-βgal. These data, as well previously published data, confirm the utility of lipid complexes for nucleic acid delivery to the lung.

Example 4

In Vivo Lipid Complex-P53 Gene Delivery to H1299 Subcutaneous Tumors

For in vivo delivery of lipid complex-P53 3-4 week old female BALB/c nude mice were subcutaneously injected with $5 \times 10^6$ H1299 tumor cells per animal. Animals were treated five days post-H1299 injection by intratumoral injection of 200 µl of lipid complex-P53 (100 µg DNA/5 mM lipid). Tumors were measured every other day. Treatment groups were 1) no treatment 2) intratumoral injection every day for 6 days with lipid complex-P53 DNA (100 µg in a 200 µl volume) 3) intratumoral injection every day for 6 days with P53 DNA (100 µg in a 200 µl volume). Tumor size was measured every other day for 16 days. Lipid complex-P53 DNA showed a significant inhibition of tumor growth compared to no treatment and DNA alone.

Example 5

Intravenous Lipid Complex-P53 Gene Delivery to H1299 Pulmonary Metastases

A lung tumor model was established by injection of $1 \times 10^6$ H1299 tumor cells in 200 µl of PBS via the tail vein of Beige/SCID mice. Three days post injection mice were administered 100 µl of lipid complex-p53 (50 µg DNA/5 mM lipids) via tail vein injection. Treatments were continued every other day for a total of 6 treatments. Animals were killed on day 21 and injected with India ink intratracheally. Pulmonary tumor nodules were visualized by developing the lungs in Feketes solution and were counted by visual inspection with the aid of a dissecting microscope. Control animals displayed approximately 400 pulmonary nodules. The lipid complex-p53 treated animals displayed approximately 10 pulmonary nodules per animal. The administration of lipid complex-P53 via tail vein injection significantly reduced tumor formation in the lungs of Beige/SCID mice.

Example 6

Intravenous Lipid Complex-P53 Gene Delivery and P53 Gene Expression Analysis in H1299 Subcutaneous Tumors A subcutaneous tumor model was established by injection of $5 \times 10^6$ H1299 tumor cells in 100 µl of PBS subcutaneously in BALB/c nude mice. Mice were administered 100 µl of lipid complex-p53 (50 µg DNA) via tail vein 5 days post subcutaneous tumor cell injection. Animals were killed 24 hours post-treatment and tissues harvested. Lung, spleen, and liver tissues were harvested and fixed in formalin. Tissue sections were analyzed using standard immuno-histochemical staining for the P53 protein. Immunostaining detected significant levels of P53 protein expression within tumor cells. No treatment and p53 DNA alone resulted in no detectable P53 protein.

Example 7

Targeting Enhanced Lipid Complex-P53 Delivery to Tumor Cells Recalcitrant to Transfection by Lipid Complex P53

Although H1299 cells were readily transfected in vitro with lipid complex-βgal, other cell lines were resistant. Tumor cell lines H322, H226Br, and A549 have been previously shown to exhibit low lipid complex transfection frequencies. In an attempt to enhance the transfection of resistant cell lines, antibody or cyclic peptide targeting moieties were associated with the lipid complex-βgal. The antibody targeting moiety is a monoclonal anti-EGF receptor antibody. The peptide targeting moiety is a cyclic peptide containing within its sequence a RGD integrin binding motif. These targeting moieties were non-covalently associated with the lipid complex. It is contemplated that a covalent attachment of the targeting moiety will further enhance the targeting efficiency of the lipid complex. Lipid complexes with associated targeting moieties demonstrated an enhanced transfection of A549 cells in vitro compared to lipid complexes without targeting moieties.

Example 8

Materials and Methods

Materials.
All lipids (DOTAP, DOPE, cholesterol) were purchased from Avanti Polar Lipids (Alabaster, Ala.). RPMI-1640 medium, Ham's/F12 medium and fetal bovine serum (FBS) were purchased from GIBCO-BRL-Life Technologies (New York, N.Y.). Polyclonal rabbit antihuman FHIT antibody and mouse antihuman p53 monoclonal antibody (BP53.12) were obtained from Zymed Laboratories (San Francisco, Calif.) and Santa-Cruz Biotechnology, Inc. (Palo Alto, Calif.) respectively.

Cell Lines and Animals.

Human non-small cell lung carcinoma cell lines, H1299 ($p53^{null}$/FHIT⁻) and A549 ($p53^+$/FHIT⁻) were obtained from American Type Culture Collection and maintained in RPMI-1640 and Hams-F12 medium supplemented with 10% FBS, 1% Glutamate and antibiotics. Murine fibrosarcoma cell line, 2337m, which is mutant for murine p53 was obtained from Dr. Isaiah J. Fidler, M.D. Anderson Cancer Center and maintained in DMEM supplemented with 10% FBS. Cells were regularly passaged and tested for presence of *mycoplasma*. 4-6 weeks old female C3H mice (NCI, Frederick, Md.), BALB/c nude (nu/nu) mice (Harlan-Sprague Dawley Inc., Indianapolis, Ind.), and SCID/Beige mice (Charles River Laboratories, Wilmington, Mass.) used in the study were maintained in a pathogen free environment and handled according to institutional guidelines established for animal care and use.

Synthesis of Liposomes and Preparation of DNA:Liposome Mixture.

Liposomes (20 mM DOTAP:Chol, and 20 mM DOTAP:DOPE) were synthesized and extruded through Whatman filters (Kent, UK) of decreasing size (1.0, 0.45, 0.2, and 0.1 μm) as described previously (Templeton, 1997). The synthesized liposomes were stored under argon gas at 4° C. DNA:liposome complexes were prepared fresh two to three hours prior to tail vein injection in mice. Briefly, DOTAP:Chol (20 mM) or DOTAP:DOPE (20 mM) stock solution and stock DNA solution diluted in 5% dextrose in water (D5W) were mixed in equal volumes to give a final concentration of 4 mM DOTAP:Chol-150 μg DNA in 300 μl final volume (ratio 1:2.6) ("Chol" refers to Cholesterol). Dilution and mixing of all reagents were at room temperature. Reagents were gently mixed in a 1.5 ml Eppendorf tube by pipetting. The DNA solution was added at the surface of the liposome and mixed rapidly up and down twice with the pipet tip. The DNA:liposome mixture thus prepared was precipitate-free and used for all in vivo experiments.

Measurement of Particle Size Analysis.

Freshly prepared DNA:liposome complexes were analyzed for mean particle size using the N4 particle size analyzer (Coulter, Miami, Fla.). The average mean particle size of the DNA:liposome complexes ranged between 300-325 nm.

In Vivo Transfection Efficiency in Subcutaneous Tumor, Normal Lung and Tumor-Bearing Lungs.

Prior to the start of the experiment, nu/nu mice were subjected to 3.5Gy of total body irradiation using a cesium source according to institutional guidelines. Mice were then injected with p53 gene-null H1299 tumor cells ($5\times10^6$/100 μl of PBS) subcutaneously on the right flank. When the tumors reached 4-5 mm³ in size, a single dose of DOTAP:Chol-DNA:liposome complex (100 μg of Lac-Z DNA) was injected intratumorally. Forty-eight hours after injection, mice were euthanized by $CO_2$ inhalation, and tumors were removed and analyzed histochemically for β-galactosidase expression (Couffinhal, 1997). Tumors were cut into 4-μm-thick sections, stained for β-galactosidase, and evaluated by light microscopy.

p53 and Fhit protein expression in tumors was determined by western blot analysis. Briefly, subcutaneous H1299 tumors injected with DOTAP:Chol-DNA:liposome complex (100 μg of Lac-Z, CAT, p53, and FHIT DNA) were harvested at 48 hours and homogenized in Laemelli buffer. Protein concentration was determined using Bio-Rad protein assay reagent (Bio-Rad, Fremont, Calif.) and 50 μg of total protein was analyzed by SDS-PAGE electrophoresis. p53 and Fhit proteins were detected using mouse antihuman p53 antibody (BP53.12) and rabbit antihuman FHIT antibody as described previously (Ji et al., 1999; Hamada et al., 1996; Sozzi et al., 1997).

To determine the transduction efficiency in normal lungs, mice were injected with DOTAP:Chol-Lac-Z or p53 DNA:liposome complexes intravenously (i.v.) via tail vein. Forty-eight hours post injection, animals were euthanized by $CO_2$ inhalation and lungs harvested and either snap frozen for β-galactosidase analysis or formalin fixed for p53 analysis. Tissue sections were cut and analyzed histochemically (β-gal) or immunohistochemically (p53) as described previously (Couffinhal, 1997). To determine the transduction efficiency in lung tumors in vivo, nude mice were injected with $1\times10^6$ A549 tumor cells suspended in 200 μl of PBS i.v. via tail vein. Two to three weeks later, a single dose of Lac-Z or FHIT DNA-DOTAP:Chol liposome complex (50 μg) or naked plasmid DNA (50 μg) was injected via tail vein. Lungs were harvested forty eight hours later and analyzed for protein expression by histochemical (β-gal) or immunohistochemical (Fhit) analysis (Couffinhal, 1997; Sozzi et al., 1997).

Evaluation of Tumor Growth and Treatments In Vivo.

Prior to the start of all experiments involving subcutaneous tumor growth and treatments, nu/nu mice were irradiated (3.5Gy) using a cesium source to enhance tumor uptake. In all the experiments, $5\times10^6$ tumor cells (H1299, A549) suspended in 100 μl sterile phosphate buffered saline (PBS) were injected into the right dorsal flank. When the tumor had reached a size of 4-5 mm³, animals were randomized into groups and treatment initiated. Intratumoral injections were performed under anesthesia using methoxyflurane (Schering Plough, Kenilworth, N.J.) as per institutional guidelines. Tumor measurements were recorded every other day without knowledge of the treatment groups, and the volume was calculated using the formula V (mm3)=a×$b^2$/2, where "a" is the largest dimension and "b" is the perpendicular diameter (Georges et al., 1993). Antitumor efficacy data are presented as cumulative tumor volumes for all animals in each group to account for both size and number of tumors.

For p53 experiments, subcutaneous H1299 tumor bearing animals were divided into three groups. Groups of eight animals were treated as follows: Group 1 received no treatment, Group 2 received naked p53 plasmid DNA (100 μg/dose) and Group 3 received DOTAP:Chol-p53 DNA:liposome complex (100 μg/dose) daily for a total of six doses. In a separate but identical experiment, an additional control group was included that received DOTAP:Chol-pAd DNA:liposome complex. All other experimental conditions and treatment schedules were identical.

For FHIT experiments, H1299 and A549 subcutaneous tumors were established in nude mice. For each tumor type, four treatment groups were established comprised of seven animals per group. Treatment groups included: Group 1 received no treatment, Group 2 received FHIT plasmid DNA (100 μg/dose), Group 3 received DOTAP:Chol-CAT DNA:liposome complex (100 μg/dose) and Group 4 received DOTAP:Chol-FHIT DNA:liposome complex (100 μg/dose). Animals were treated daily for a total of six doses. In all experiments, statistical differences in tumor size were determined using the Student's t test.

Evaluation of lung metastases and treatments in vivo. To establish lung metastases, female SCID/Beige mice were injected intravenously via tail vein with $10^6$ H1299 tumor cells suspended in 200 µl of sterile PBS. Three days later, mice were divided into six groups and treated as follows: no treatment (Group 1), naked p53 plasmid DNA (Group 2), DOTAP-DOPE-p53 DNA:liposome complex (Group 3), DOTAP:Chol-CAT DNA:liposome complex (Group 4), non-extruded DOTAP:Chol-p53 DNA:liposome complex (Group 5) and DOTAP:Chol-p53 DNA:liposome complex (Group 6). There were eight mice in each group. Mice were treated with 50 µg of plasmid DNA or 50 µg DNA:liposome complex i.v. via tail vein using a 27 gauge needle daily for a total of six doses. Two weeks following the last dose, animals were euthanized by $CO_2$ inhalation. Lungs from each of the mice from the six groups were injected intra-tracheally with India ink and fixed in Feketes solution (Kataoka et al., 1998). The therapeutic effect of systemic p53 gene treatment was determined by counting the number of metastatic tumors in each lung under a dissecting microscope without knowledge of the treatment groups. The data were analyzed and interpreted as statistically significant if the p value was <0.05 by the Mann-Whitney rank-sum test.

The A549 tumor model was used to determine the therapeutic effect of p53 and FHIT tumor suppressor genes on p53 wild type lung tumor cells. Mice (nu/nu) were injected with A549 tumor cells ($1 \times 10^6$) i.v via tail vein. On day 6, mice were divided into four groups (n=6 or 8 animals per group) and received the following treatment. Group 1 received no treatment, group 2 received p53 or FHIT plasmid DNA, group 3 received extruded DOTAP:Chol-CAT DNA:liposome complex and group 4 received extruded DOTAP:Chol-p53 DNA:liposome complex or DOTAP:Chol-FHIT DNA:liposome complex. Animals were treated daily for a total of six doses (50 µg/dose). Following the last dose, mice were euthanized and therapeutic effect of p53 DNA:liposome and FHIT DNA:liposome complex treatments determined as described above for the H1299/SCID/Beige model.

Immunohistochemical Analysis.

Subcutaneous H1299 tumors established in nu/nu mice that were either not treated or treated with p53 plasmid DNA or treated with p53 DNA:liposome complex were harvested and fixed in 4% buffered formalin, paraffin embedded and cut as 4 µm thick sections. Tissue sections were stained for p53 gene expression as previously described (Fujiwara et al., 1993; Fujiwara et al., 1995). The number of tumor cells staining positive for p53 were analyzed under bright field microscopy and quantitated without prior knowledge of the treatment groups. A total of at least five fields per specimen were analyzed. To determine the fate of tumor cells following treatment, subcutaneous tumors and tumor bearing lung sections were stained for apoptotic cell death using terminal deoxynucleotide transferase (Tdt) (Boehringer Mannheim) and counterstained with methylene blue or methyl green as described previously (Fujiwara et al., 1993; Fujiwara et al., 1995). In all the staining procedures, appropriate negative controls were included.

Histopathology.

To determine the therapeutic effect of the p53 gene on metastatic lung tumors, tumor bearing lungs were harvested from nu/nu mice at 21 days post treatment and evaluated histopathologically for tumor size, viability and mitotic index. Analysis was done by a pathologist without prior knowledge of the treatment groups.

Survival Experiments.

To determine the efficacy of systemic treatment, survival experiments were performed using the two metastatic lung tumor (H1299, A549) models. Briefly, female SCID/Beige mice were injected with $10^6$ H1299 tumor cells via the tail vein. Six days later, mice were divided into four groups of six mice each as follows: Group 1 received no treatment, Group 2 received naked p53 plasmid DNA, Group 3 received DOTAP:Chol-CAT DNA:liposome complex, and Group 4 received DOTAP:Chol-p53 DNA:liposome complex. The treatment schedule consisted of six daily injections of naked plasmid DNA or DNA:liposome complex in 100 µl volumes (50 µg DNA/dose). Mice were monitored daily following the last injection. Moribund animals were euthanized by $CO_2$ inhalation. Lungs, heart, liver, spleen, brain, kidney, colon, ovaries, pancreas, and bone from each animal were removed and analyzed histopathologically for the presence of disseminated tumors and for treatment associated toxicity. Statistical differences in actuarial survival curves were analyzed using the Kaplan-Meier survival estimation and Wilcoxon signed rank tests.

The A549 lung metastatic tumor model was used to evaluate the effect of the DOTAP:Chol-p53 DNA:liposome complex on tumors that have the wild-type p53 gene. Briefly, nu/nu mice were injected with $10^6$ A549 tumor cells i.v. via the tail vein. Six days later, mice were divided into four groups (groups 1 to 4) of seven mice each. The experimental conditions and treatment schedule were identical to those used for the H1299-SCID/Beige lung tumor model. The effect of delivering DOTAP:Chol-p53 DNA:liposome complex on survival was calculated using the Kaplan-Meier survival estimation and the Wilcoxon rank test.

Statistical Analysis:

The statistical significance of the experimental results was calculated using Student's t-test for tumor measurements, Mann-Whitney rank-sum test for lung metastases, Wilcoxon log rank test and Kaplan-Meier survival test for animal survival experiments.

Example 9

In Vivo Transfection in Normal Lung, Primary Tumor Xenografts and Experimental Metastatic Lung Tumors The ability of extruded DOTAP:Chol liposomes to effectively transfect and deliver plasmid DNA into normal lung, subcutaneous lung tumor xenografts, and experimental metastatic lung tumors was determined using expression plasmids encoding the bacterial β-galactosidase (Lac-Z), human p53, or human Fhit protein. 48 hours following a single i.v. tail vein injection of DOTAP:Chol liposomes complexed with Lac-Z plasmid DNA or human p53 plasmid DNA (50 µg of DNA) that were 300-325 nm in size, alveolar epithelial cells (type II pneumocytes) and endothelial cells in the lung were largely observed to produce β-galactosidase or p53 protein. Few alveolar macrophages expressed the transgene. In contrast, no gene expression was observed in animals injected with naked p53 plasmid DNA (50 µs).

To determine whether gene expression could also be achieved in solid primary tumors, human H1299 lung tumors were established subcutaneously in nude mice. Forty-eight hours following a single intratumoral injection of DOTAP:Chol-LacZ DNA:liposome complex, 25% of the tumor cells produced β-galactosidase, as shown by histochemical staining. In contrast, no β-galactosidase production was observed in the untreated control tumors. Intratumoral injection of DOTAP:Chol liposomes complexed to FHIT (50 µg of DNA) resulted in production of Fhit protein, as determined by western blot analysis. Tumor-bearing animals injected with DOTAP:Chol liposomes complexed to CAT DNA served as controls. Similarly, p53 protein expression was observed by western blot analysis.

The ability to transfect experimental human A549 lung metastatic tumors established in nude mice was also evaluated. A single tail vein injection of DOTAP:Chol liposomes complexed to Lac-Z or FHIT plasmid DNA (50 µg) into lung tumor-bearing mice resulted in 10% of the tumor cells producing β-galactosidase and Fhit protein at 48 hours.

Example 10

In Vivo Evaluation of Local Tumor Growth Suppression by P53 and Fhit

The ability of the DOTAP:Chol-p53 DNA:liposome complex to suppress the growth of p53 gene-null H1299 human lung subcutaneous tumors in nu/nu mice was assessed. Tumor-bearing mice were divided into three groups: one receiving no treatment, one treatment with naked p53 plasmid DNA, and one treatment with the DOTAP:Chol-p53 DNA liposome complex daily for a total of six doses (100 µg/dose). Tumor growth was significantly inhibited (p=0.001) in mice treated with the DOTAP:Chol-p53 liposome complex (FIG. 1a) as compared with tumor growth in the no treatment and p53 plasmid DNA control groups.

To further demonstrate the specific tumor-suppressive effects of the p53 gene delivered by DOTAP:Chol liposomes, in a separate set of experiments, subcutaneous H1299 tumor-bearing animals were divided into three groups, one receiving no treatment, one treatment with DOTAP:Chol liposome complexed to irrelevant plasmid DNA (pAd) and one treatment with the DOTAP:Chol-p53 DNA complex daily for a total of six doses (100 µg/dose). Significant inhibition of tumor growth was not observed in animals that were either not treated or treated with the DOTAP:Chol liposome complexed to irrelevant plasmid DNA (FIG. 1b). In contrast, animals treated with the DOTAP:Chol-p53 DNA:liposome complex showed significant tumor inhibition (p=0.01).

Figure 1C:
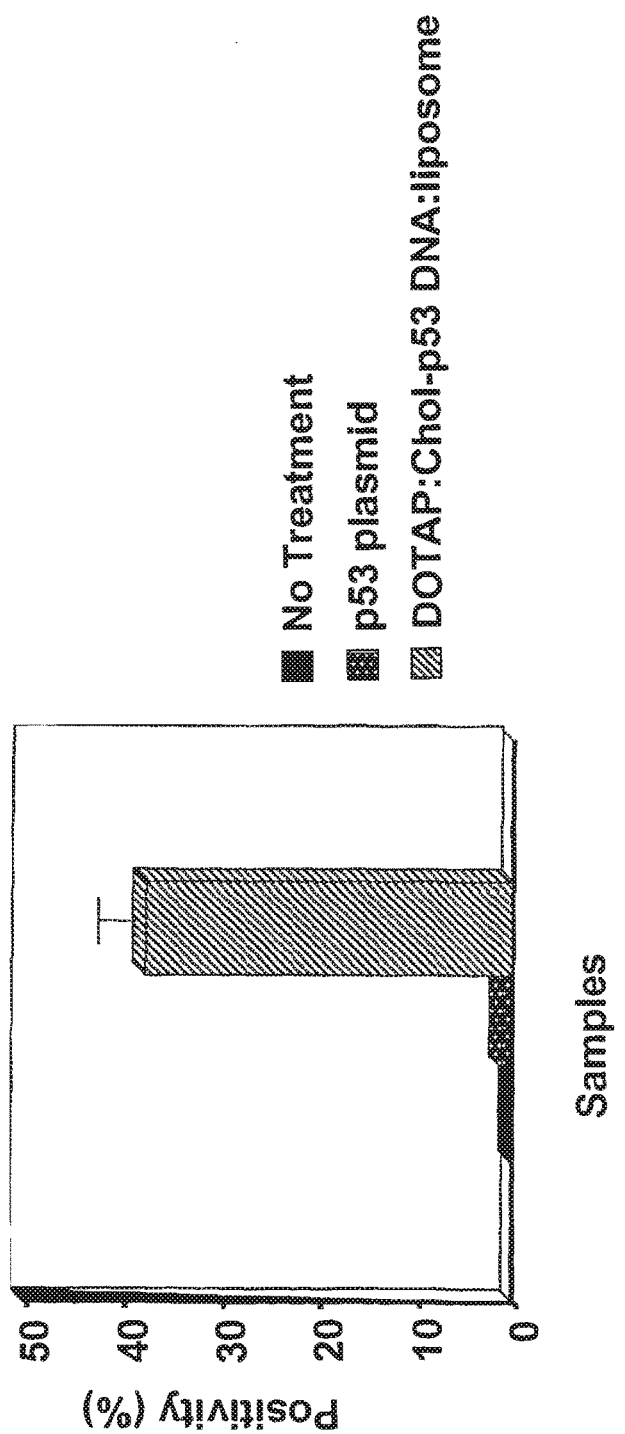
Figure 1D:
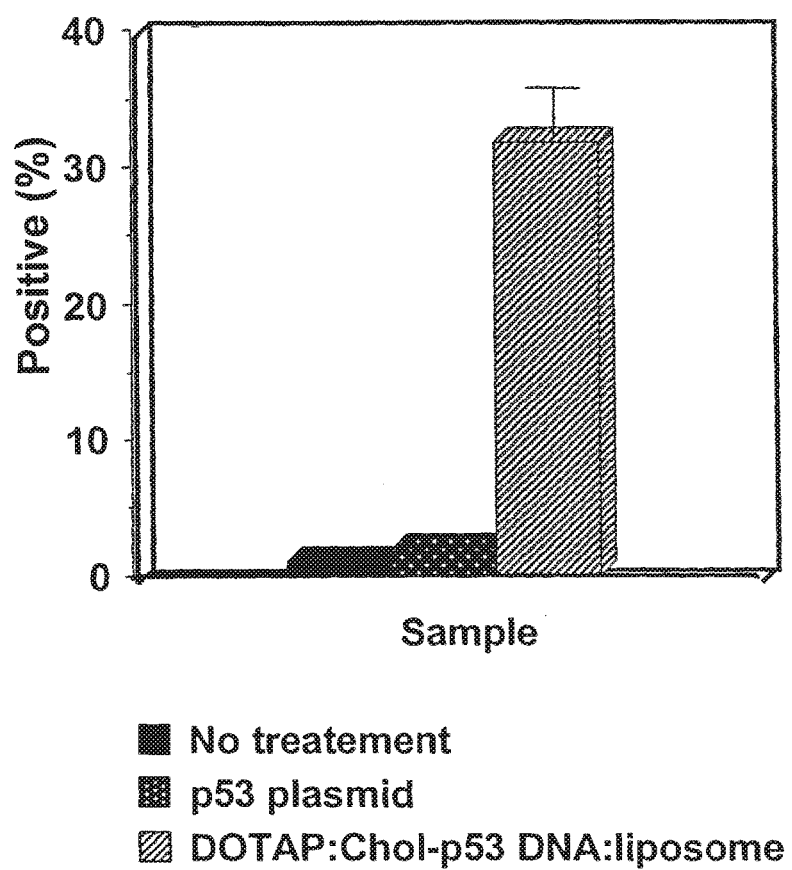

Further evidence that the observed therapeutic effect was due to p53 gene expression was obtained by removing subcutaneous tumors 48 hours after injection and analyzing them for p53 gene expression by immunohistochemistry. p53 gene expression was seen in 39% of tumor cells in animals receiving the DOTAP:Chol-p53 liposome complex, (FIG. 1c) (p=0.001), as compared with the percentage in control tumors that were either not treated or treated with p53 plasmid DNA. Analysis of apoptotic tumor cell death showed that 32% of the tumor cells in mice receiving the DOTAP:Chol-p53 liposome complex were positive in TUNEL studies (p=0.001) (FIG. 1d). Tumors from control mice that were either untreated or treated with p53 plasmid DNA showed minimal apoptotic cell death (FIG. 1d).

Figure 1E:
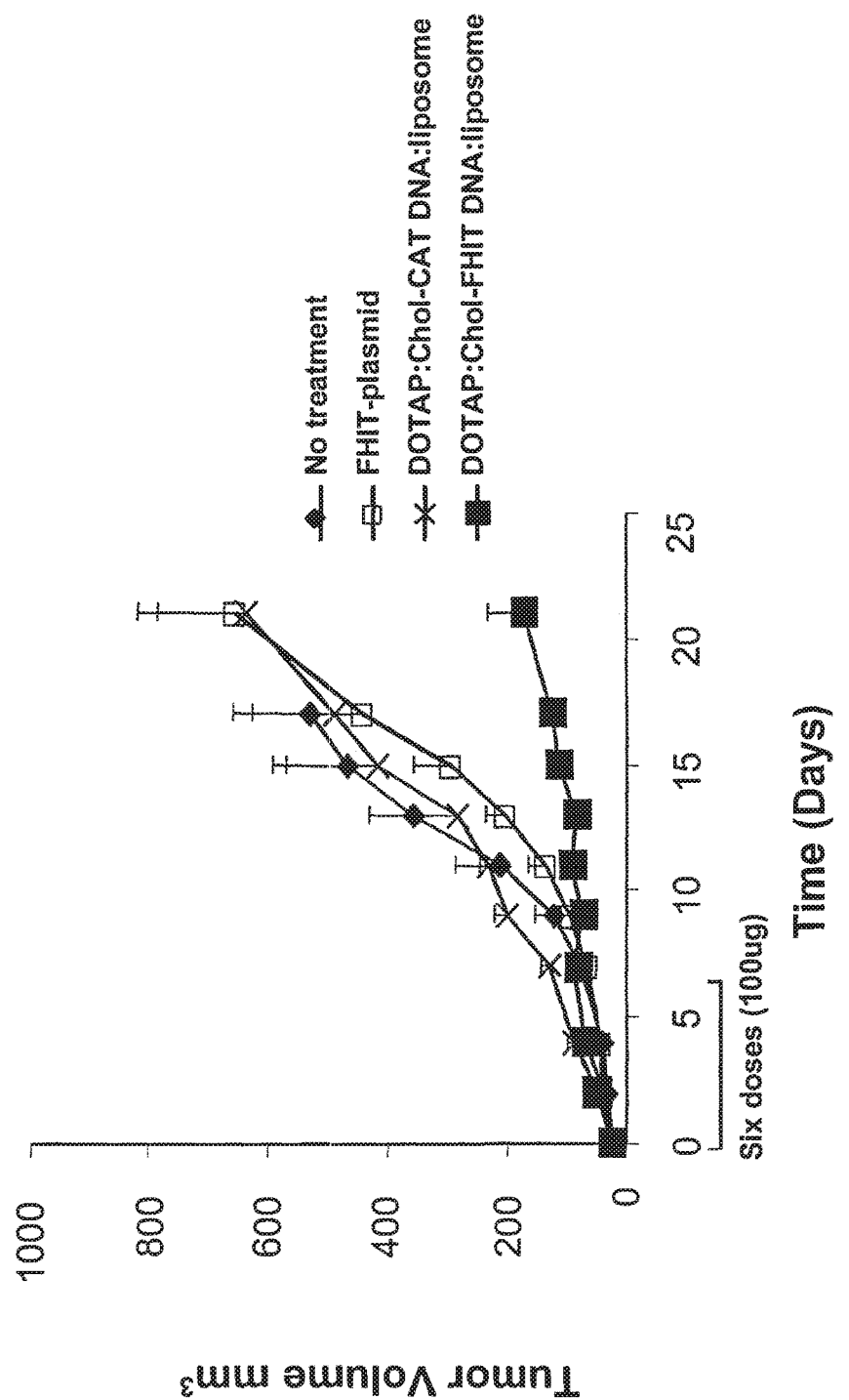
Figure 1F:
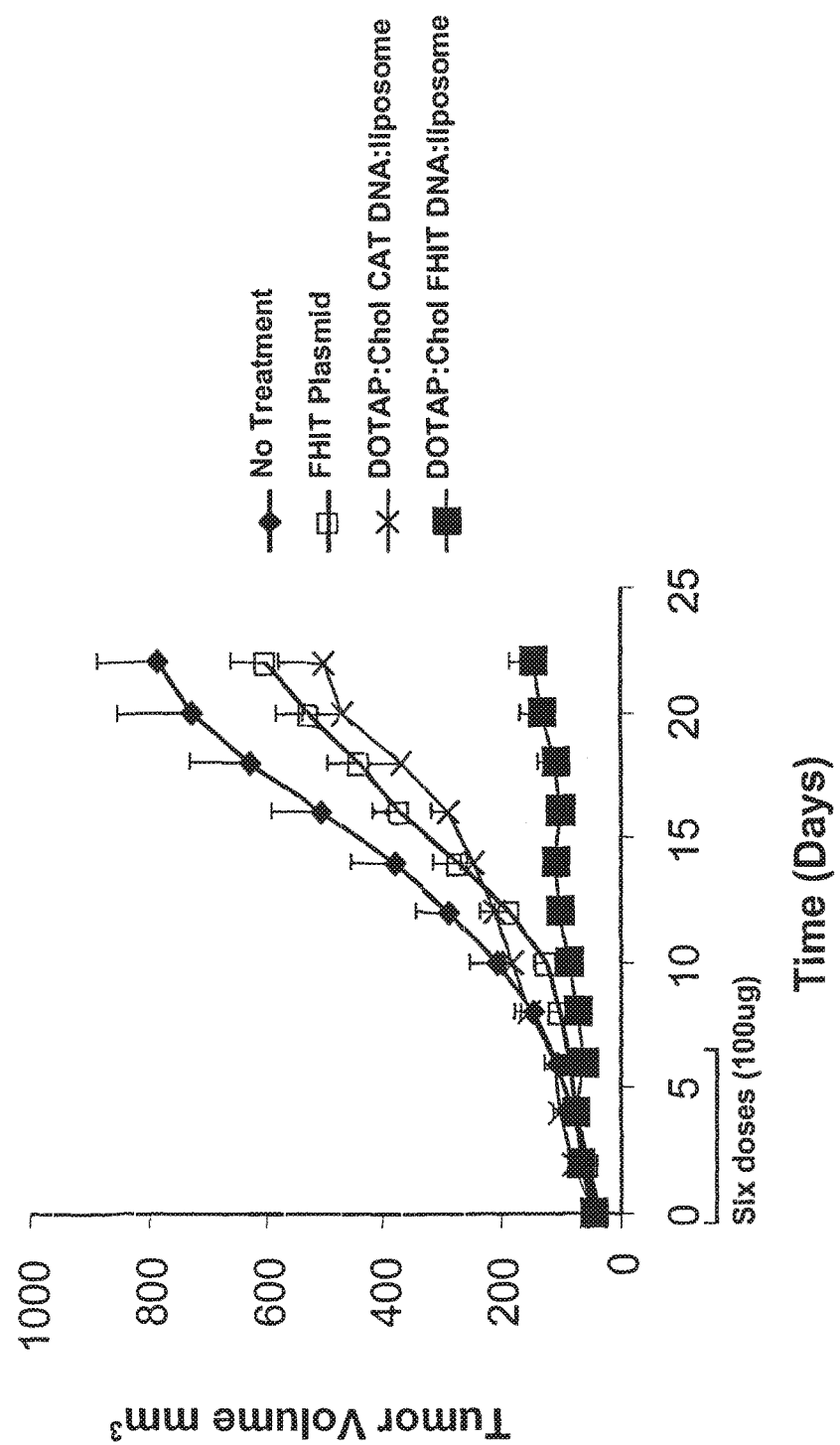

The therapeutic effect of the FHIT tumor suppressor gene on H1299 and A549 subcutaneous tumors in nude mice was similarly evaluated. Mice bearing each tumor cell type (H1299 and) A549) were divided into four groups: one receiving no treatment, one treatment with naked FHIT plasmid DNA, one treatment with the DOTAP:Chol-CAT DNA liposome complex, and one treatment with the DOTAP:Chol-FHIT DNA liposome complex daily for a total of six doses (100 µg/dose). A significant growth inhibition of H1299 tumors (p=0.02) (FIG. 1e) and A549 tumors (p=0.001) (FIG. 1f) was observed in mice treated with the DOTAP:Chol-FHIT DNA liposome complex compared with the tumor growth in the three control groups for each tumor type.

Example 11

Figure 2A:
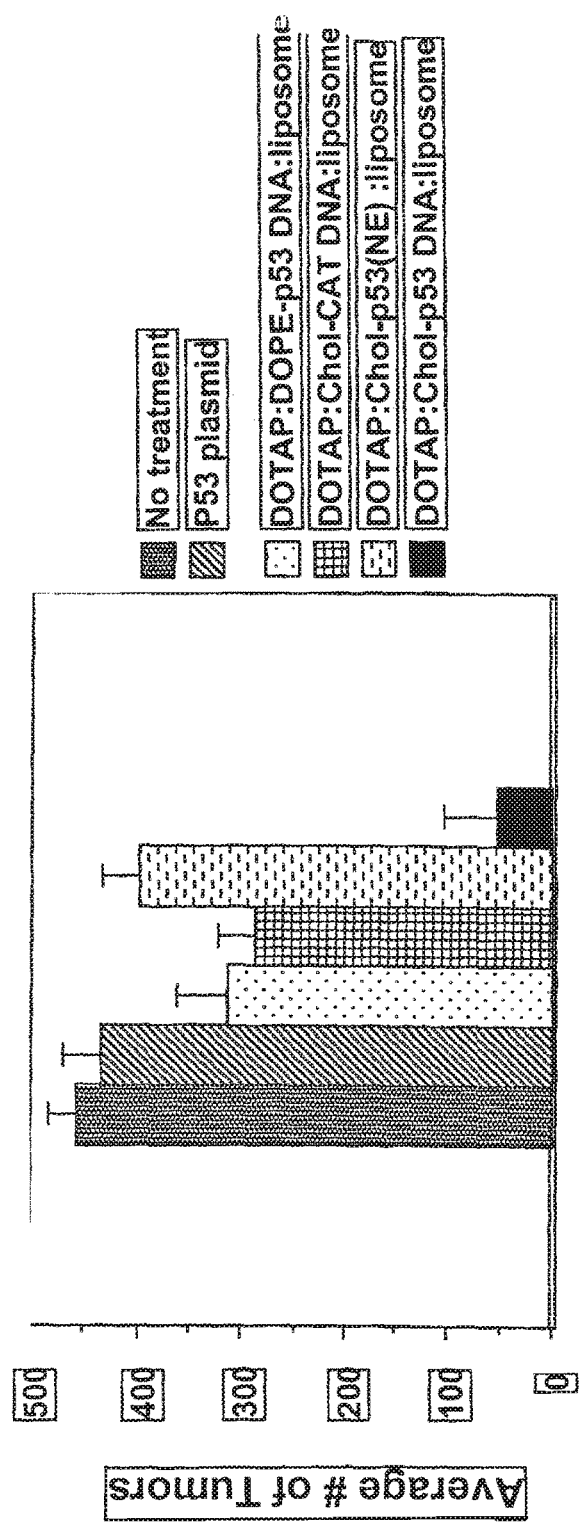
FIGS. 2A-C. Effects of intravenous treatment with extruded DOTAP:Chol-p53 DNA:liposome complex or DOTAP:Chol-FHIT DNA:liposome complex on lung metastases.

In Vivo Evaluation of P53 and Fhit Plasmid DNA Complexed to DOTAP:Chol Liposomes for Treatment of Experimental Lung Metastases The effectiveness of extruded DOTAP:Chol liposomes, over non-extruded DOTAP:Chol liposomes, and another conventional liposome formulation (DOTAP:DOPE) was compared in a therapeutic xenograft model of human lung metastases using the H1299 and A549 human lung cancer cells. There was a significant reduction (p<0.001) in the number of metastases in the lungs from p53 gene-null H1299 lung tumor-bearing SCID/Beige mice receiving the extruded DOTAP:Chol-p53 DNA:liposome complex (FIG. 2a) as compared with the number in mice receiving no treatment, p53 plasmid DNA, the extruded DOTAP:Chol-CAT DNA:liposome complex, the DOTAP:DOPE-p53 DNA:liposome complex, or the nonextruded DOTAP:Chol-p53 DNA:liposome complex. In addition, metastatic tumor growth was inhibited in animals treated with the extruded DOTAP:Chol-CAT DNA:liposome complex and the DOTAP:DOPE-p53 DNA:liposome complex compared with tumor growth in mice receiving no treatment, p53 plasmid DNA, or nonextruded DOTAP:Chol p53 DNA complex. However, the tumor inhibitory effects were minimal.

Figure 2B:
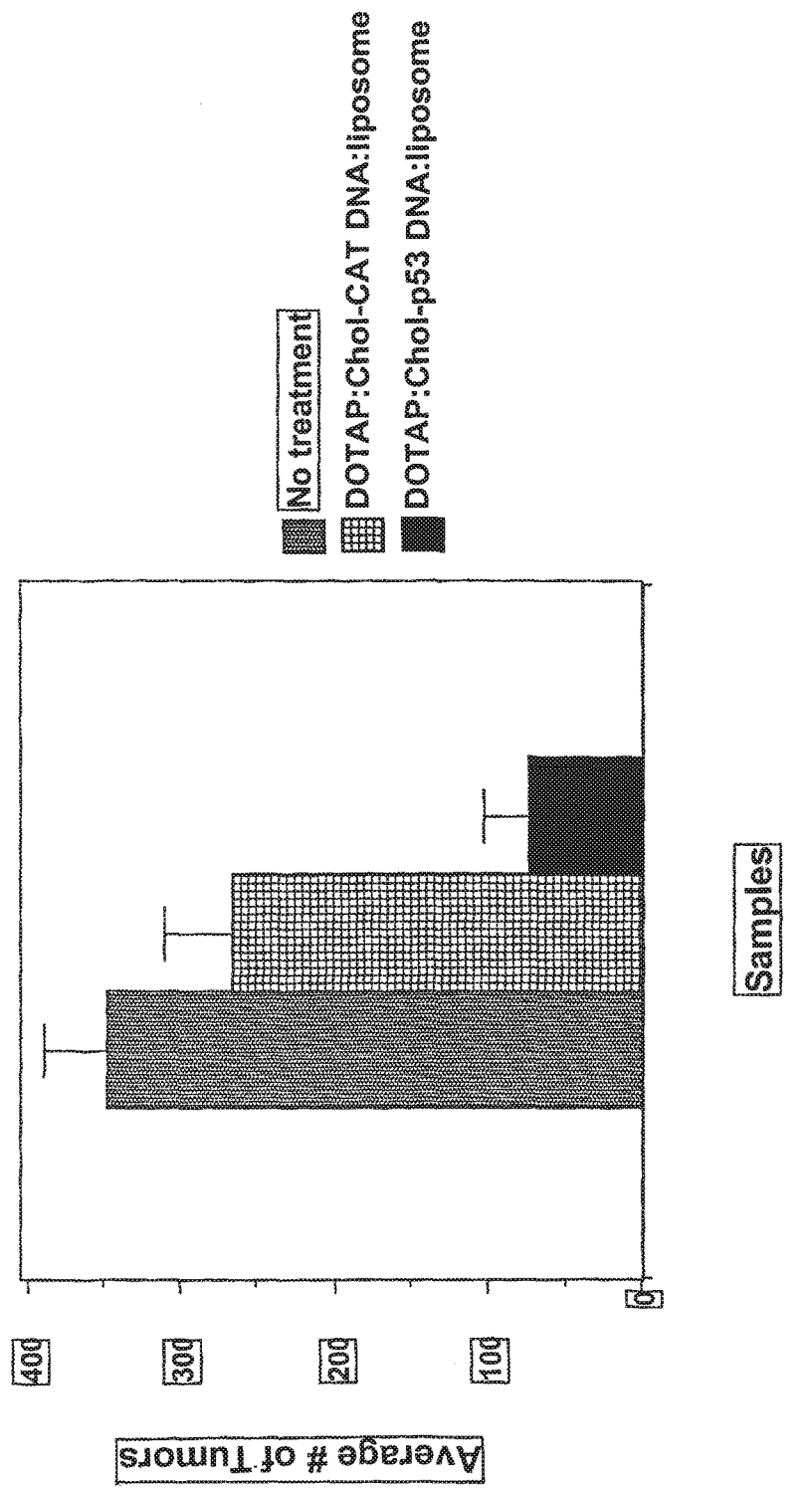

To determine if the observed p53 gene-mediated tumor inhibitory effects were restricted to p53 gene mutated or null tumors, the effects of the DOTAP:Chol-p53 DNA:liposome complex were studied in A549 tumor cells, which are homozygous for the wild-type p53 gene and form lung metastases following tail vein injection in nu/nu mice. A significant reduction (p=0.001) in the number of metastases was observed in mice treated with the extruded DOTAP:Chol-p53 DNA:liposome complex compared with the number of metastases in control mice that were either not treated or treated with the DOTAP:Chol-CAT DNA:liposome complex (FIG. 2b), thus ruling out the possibility that the p53 gene mediated inhibition was limited to p53 gene mutated or null tumors. No significant difference was observed in the number of metastases between the two control groups.

Figure 2C:
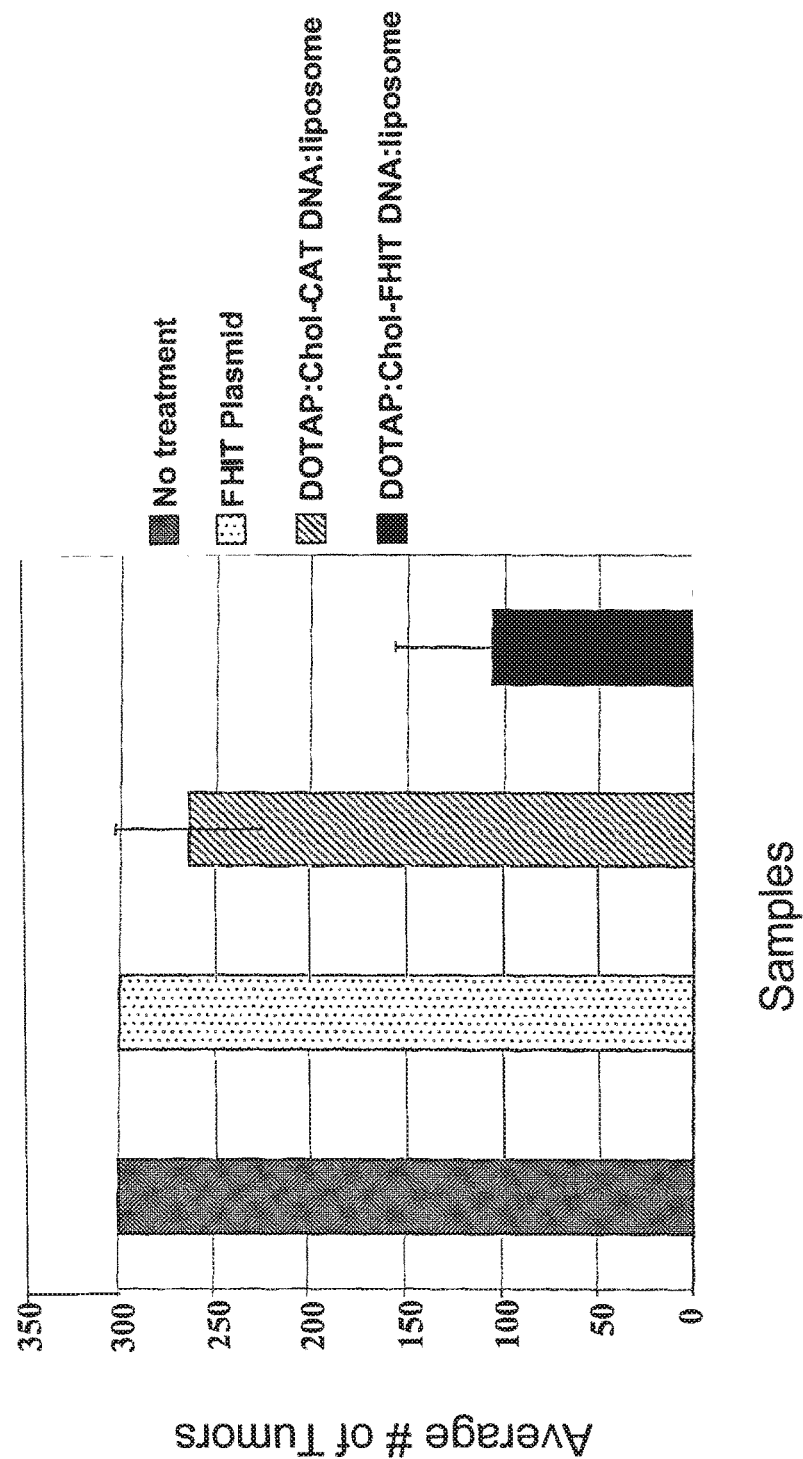

The ability of the FHIT tumor suppressor gene to inhibit lung metastases formed by A549 tumor cells in nude mice was also evaluated. A significant reduction (p=0.007) in the number of tumor metastases was observed in animals treated with the DOTAP:Chol-FHIT DNA:liposome complex (FIG. 2c). In contrast, control animals that were not treated, treated with FHIT plasmid DNA, or treated with the DOTAP:Chol-CAT DNA:liposome complex showed no significant reduction in the number of tumor metastases.

Example 12

Treatment of Lung Tumors with DOTAP:Chol-P53 DNA:Liposome Complex Results in Apoptotic Tumor Cell Death To determine the fate of tumor cells after treatment with the DOTAP:Chol-p53 DNA:liposome complex, A549 lung tumors from nu/nu mice were analyzed histologically, and apoptotic cell death was assessed by TUNEL staining. Histopathological examination of the lung sections from mice treated with the DOTAP:Chol-p53 DNA:liposome complex showed the presence of very few metastases that were small and contained only a few viable tumor cells. In addition, the number of tumor metastases in the lungs of these animals was significantly less than that in control animals. Further, apoptotic cell death had occurred in these tumors, as demonstrated by TUNEL staining. In contrast, lungs from control mice that received no treatment showed several large tumors with numerous mitoses and no evidence of apoptotic cell death.

Example 13

Animal Survival in a Model of Disseminated Human Lung Cancer

Figure 3A:
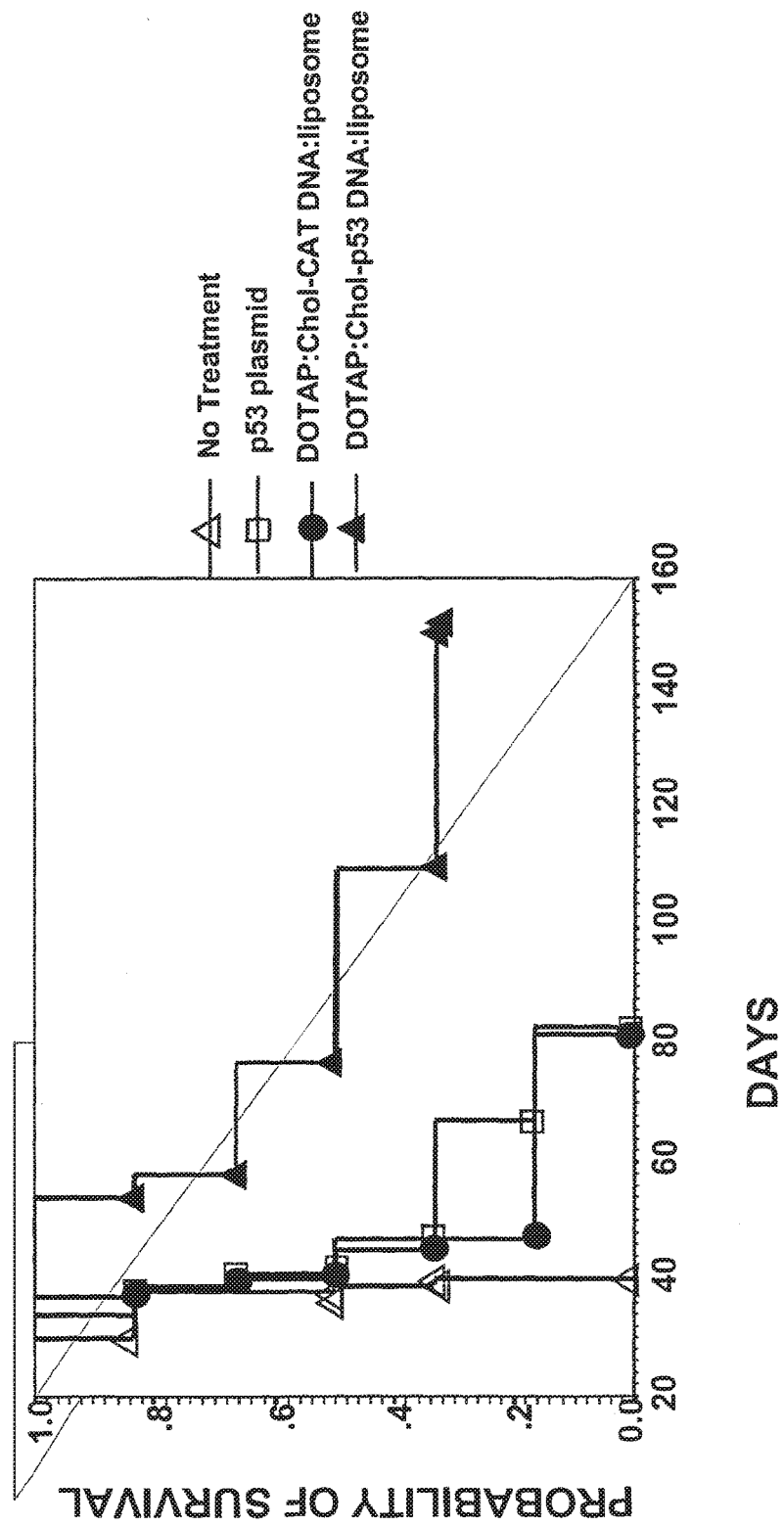
FIGS. 3A-B. Survival experiments in mice treated with DOTAP:Chol-p53 DNA:liposome complex treatments. Female SCID/Beige mice were injected with $10^6$ H1299 tumor cells (six animals/group) and BALB/c nu/nu mice were injected with $10^6$ A549 tumor cells (seven animals/group) via the tail vein. Animals were divided into four groups and treated daily, as follows: no treatment, treatment with p53 plasmid DNA, treatment with the DOTAP:Chol-CAT DNA:liposome complex, or treatment with the DOTAP:Chol-p53 DNA:liposome complex. Animals in each group received a total of six doses (50 µg/dose) and were monitored daily to assess morbidity and mortality. Animal survival was estimated using the Kaplan-Meier and Wilcoxon signed rank tests. Survival was significantly increased in H1299 lung tumor-bearing animals treated with the DOTAP:Chol-p53 DNA:liposome complex ($p=0.001$) as compared with survival in control animals that received either no treatment or treatment with p53 plasmid DNA or the DOTAP:Chol-CAT DNA:liposome complex (FIG. 3A). H1299 injected animals showed tumor dissemination to various organs and tissues, including the cervical lymph nodes, colon, mesentery, and liver. Survival was also significantly increased in A549 lung tumor-bearing mice treated with the DOTAP:Chol-p53 DNA:liposome complex ($p=0.04$) as compared with survival in animals from control groups (FIG. 3B).

To determine the efficacy of the systemically administered extruded liposomal tumor suppressor gene complex, survival experiments were performed using the H1299 and A549 lung metastasis tumor models. H1299 lung tumor-bearing SCID/Beige mice were divided into four groups, as follows: no treatment (Group 1), p53 plasmid DNA (Group 2), DOTAP:Chol-CAT DNA:liposome complex (Group 3), and DOTAP:Chol-p53 DNA:liposome complex (Group 4). Animals were injected daily via tail vein for a total of six doses (50 µg/dose) and monitored daily following the last treatment to assess morbidity and mortality. Mice from Groups 1, 2, and 3 died from the tumor burden between 30 and 60 days after tumor cell injection (median survival time: 38 days in Group 1, 40 days in Group 2, and 41 days in Group 3). In contrast, mice treated with the DOTAP:Chol-p53 DNA:liposome complex (Group 4) survived for significantly longer period (median survival: 76 days; p=0.001). In fact, 33% of mice from Group 4 were still alive on day 150 at the end of the experiment (FIG. 3a). Postmortem analysis of organs from animals in all four groups showed no treatment related toxicity. However, dissemination of lung tumors to multiple organs and sites that included the cervical lymph node, intestine, mesenteric lymph nodes, liver, kidney, spleen, pancreas, adrenal, ovaries, uterus, peritoneal cavity with ascites, and bone was revealed.

Figure 3B:
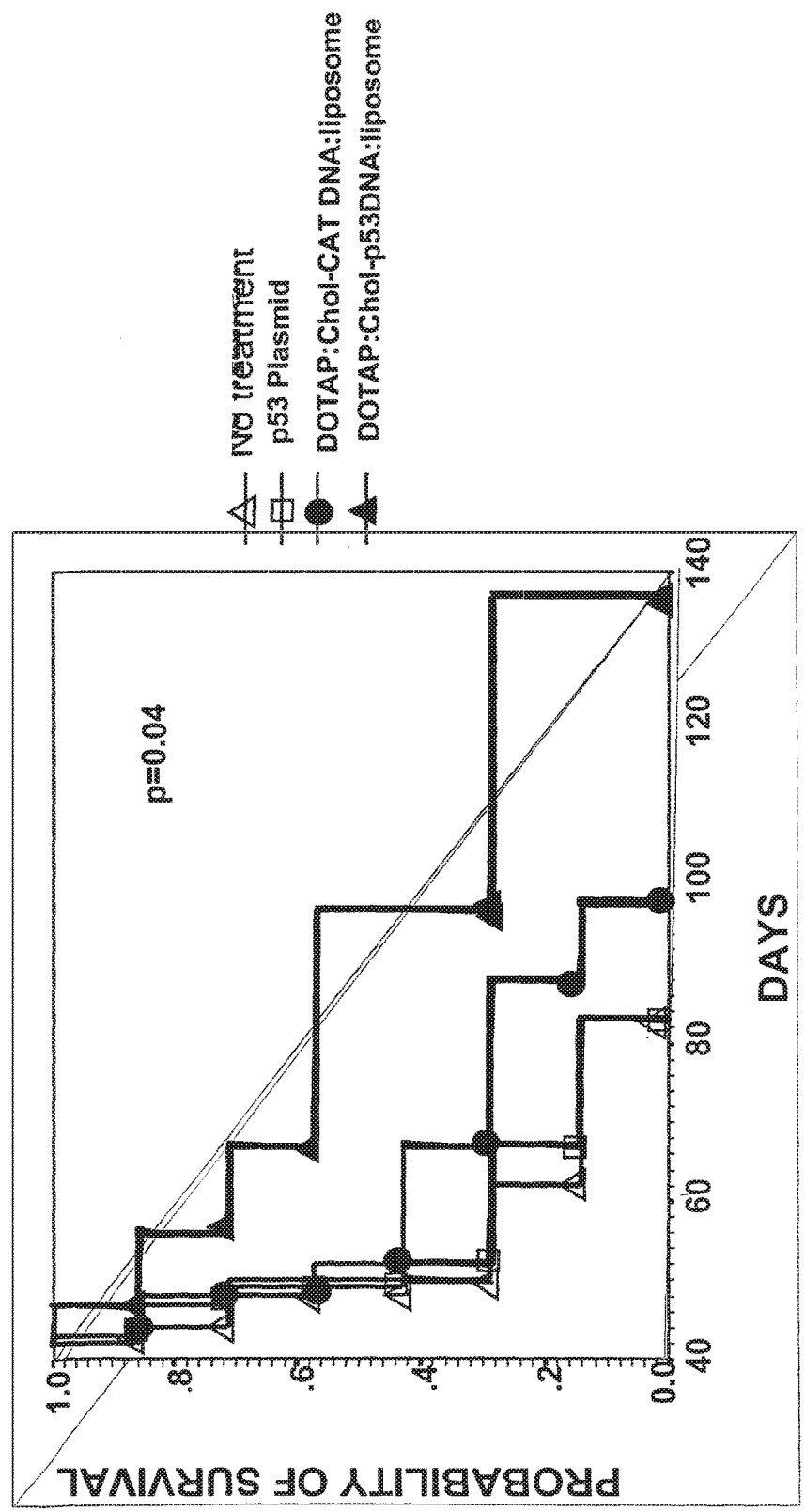

Survival in A549 lung tumor-bearing nu/nu mice was also evaluated. Following tumor cell injection, animals were divided into four groups, as follows: no treatment (Group 1), p53 plasmid DNA (Group 2), DOTAP:Chol-CAT DNA:liposome complex (Group 3), and DOTAP:Chol-p53 DNA:liposome complex (Group 4). The treatment schedule was identical to that followed in the H1299/SCID/Beige model. Mice in Group 4, which received the DOTAP:Chol-p53 DNA:liposome complex, showed prolonged survival (median survival, 96 days; p=0.04) as compared with mice in the three control groups (median survival: 50 days in Group 1, 49 days in Group 2, and 52 days in Group 3) (FIG. 3b). Histopathological analysis of various organs revealed extensive tumor spread in the lungs of all four groups of animals, but dissemination to other organs was not observed in animals in any of the four groups. In addition, treatment associated toxicity was not observed in animals from any of the four groups.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents, which are both chemically and physiologically related, may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,399,363, issued Mar. 21, 1995.
U.S. Pat. No. 5,401,511, issued Mar. 28, 1995.
U.S. Pat. No. 5,432,260, issued Jul. 11, 1995.
U.S. Pat. No. 5,466,468, issued Nov. 14, 1995.
U.S. Pat. No. 5,543,158, issued Aug. 6, 1996.
U.S. Pat. No. 5,603,872, issued Feb. 18, 1997.
U.S. Pat. No. 5,633,016, issued May 27, 1997.
U.S. Pat. No. 5,641,515, issued Jun. 24, 1997.
U.S. Pat. No. 5,656,016, issued Aug. 12, 1997.
U.S. Pat. No. 5,697,899, issued Dec. 16, 1997.
U.S. Pat. No. 5,739,169, issued Apr. 14, 1998.
U.S. Pat. No. 5,770,219, issued Jun. 23, 1998.
U.S. Pat. No. 5,779,708, issued Jul. 14, 1998.
U.S. Pat. No. 5,783,208, issued Jul. 21, 1998.
U.S. Pat. No. 5,786,214, issued Jul. 28, 1998.
U.S. Pat. No. 5,797,898, issued Aug. 25, 1998.
U.S. Pat. No. 5,798,339, issued Aug. 25, 1998.
U.S. Pat. No. 5,801,005, issued Sep. 1, 1998.
U.S. Pat. No. 5,811,128, issued Sep. 22, 1998.
U.S. Pat. No. 5,824,311, issued Oct. 20, 1998.
U.S. Pat. No. 5,824,346, issued Oct. 20, 1998.
U.S. Pat. No. 5,830,880, issued Nov. 3, 1998.
U.S. Pat. No. 5,846,225, issued Dec. 8, 1998.
U.S. Pat. No. 5,846,233, issued Dec. 8, 1998.
U.S. Pat. No. 5,846,945, issued Dec. 8, 1998.
U.S. Pat. No. 5,849,718, issued Dec. 15, 1998.
U.S. Pat. No. 5,871,727, issued Feb. 16, 1999.
U.S. Pat. No. 5,879,703, issued Mar. 9, 1999.
U.S. Pat. No. 5,889,155, issued Mar. 30, 1999.
U.S. Pat. No. 5,902,584, issued May 11, 1999.
WO 98/07408
WO 99/18933
Aksentijevich et al., *Human Gene Ther.* 7:1111, 1996.
Arap et al., *Cancer Res.*, 55:1351-1354, 1995.
Angel et al., *Cell*, 49:729, 1987b.
Angel et al., *Mol. Cell. Biol.*, 7:2256, 1987a.
Atchison and Perry, *Cell*, 46:253, 1986.
Atchison and Perry, *Cell*, 48:121, 1987.
Austin-Ward, Villaseca, "Gene therapy and its applications," *Rev. Med. Chil.*, 126(7):838-45, 1998.
Bajorin et al., *Proc. Annu. Meet. Am. Soc. Clin. Oncol.*, 7:A967, 1988.
Bakhshi et al., "Cloning the chormosomal breakpoint of t (14;18) human lymphomas: clustering around JH on chromosome 14 and near a transcriptional unit on 18," *Cell*, 41(3):899-906, 1985.
Banerji et al., *Cell*, 35:729, 1983.
Berkhout et al., *Cell*, 59:273, 1989.
Blanar et al., *EMBO* 1, 8:1139, 1989.
Bodine and Ley, *EMBO J.*, 6:2997, 1987.
Boshart et al., *Cell*, 41:521, 1985.
Bosze et al., *EMBO J.*, 5:1615, 1986.

Bourlais et al., "Opthalmic drug delivery systems-recent advances." *Prog. Retin. Eye Res.*, 17:33-58, 1998.

Braddock et al., *Cell*, 58:269, 1989.

Brizel, "Future directions in toxicity prevention," *Semin. Radiat. Oncol.*, 8(4 Suppl. 1):17-20, 1998.

Bukowski, Rayman, Uzzo, Bloom, Sandstrom, Peereboom, Olencki, Budd, McLain, Elson, Novick, Finke, "Signal transduction abnormalities in T lymphocytes from patients with advanced renal carcinoma: clinical relevance and effects of cytokine therapy," *Clin. Cancer Res.*, 4(10):2337-47, 1998.

Bulla and Siddiqui, *J. Virol.*, 62:1437, 1986.

Bussemakers et al., *Cancer Res.*, 52:2916-2922, 1992.

Caldas et al., *Nat. Genet.*, 8:27-32, 1994.

Campbell and Villarreal, *Mol. Cell. Biol.*, 8:1993, 1988.

Campere and Tilghman, *Genes and Dev.*, 3:537, 1989.

Campo et al., *Nature*, 303:77, 1983.

Celander and Haseltine, *J. Virology*, 61:269, 1987.

Celander et al., *J. Virology*, 62:1314, 1988.

Chandler et al., *Cell*, 33:489, 1983.

Chang et al., *Mol. Cell. Biol.*, 9:2153, 1989.

Chatterjee et al., *Proc. Nat'l Acad. Sci. USA.*, 86:9114, 1989.

Cheng et al., *Cancer Res.*, 54:5547-5551, 1994.

Choi et al., *Cell*, 53:519, 1988.

Christodoulides, Brooks, Rattue, Heckels, "Immunization with recombinant class 1 outer-membrane protein from *Neisseria meningitidis*: influence of liposomes and adjuvants on antibody avidity, recognition of native protein and the induction of a bactericidal immune response against meningococci," *Microbiology*, 144(Pt 11):3027-37, 1998.

Cleary et al., "Detection of a second t(14;18) breakpoint cluster region in human follicular lymphomas," *J. Exp. Med.*, 164(1):315-20, 1986.

Cleary and Sklar, "Nucleotide sequence of a t(14;18) chromosomal breakpoint in follicular lymphoma and demonstration of a breakpoint-cluster region near a transcriptionally active locus on chromosome 18," *Proc. Nat'l. Acad. Sci. USA*, 82(21):7439-43, 1985.

Cohen, Hirschhorn, Horowitz, Rubinstein, Polmar, Hong. and Martin, Jr., *Proc. Nat'l Acad. Sci.* USA 75, 472-476, 1978.

Couffinhal, T. et al. Histochemical staining following LacZ gene transfer underestimates transfection efficiency. *Hum. Gene Ther.* 8, 929-934 (1997). Costa et al., *Mol. Cell. Biol.*, 8:81, 1988.

Cripe et al., *EMBO* 1, 6:3745, 1987.

Culotta and Hamer, *Mol. Cell. Biol.*, 9:1376, 1989.

Culver et al., "In vivo gene transfer with retroviral vector-producer cells for treatment of experimental brain tumors," *Science*, 256:1550-1552, 1992.

Curran, "Radiation-induced toxicities: the role of radioprotectants," *Semin. Radiat. Oncol.*, 8(4 Suppl. 1):2-4, 1998.

Dandolo et al., *J Virology*, 47:55, 1983.

Davidson, Musk, Wood, Morey, Ilton, Yu, Drury, Shilkin, Robinson, "Intralesional cytokine therapy in cancer: a pilot study of GM-CSF infusion in mesothelioma," *J. Immunother.*, 21(5):389-98, 1998.

De Villiers et al., *Nature*, 312:242, 1984.

Deschamps et al., *Science*, 230:1174, 1985.

Edbrooke et al., *Mol. Cell. Biol.*, 9:1908, 1989.

Edelman and Crossin, *Annu. Rev. Biochem.*, 60:155-190, 1991.

Edelman, *Annu. Rev. Biochem.*, 54:135-169, 1985.

Edlund et al., *Science*, 230:912, 1985.

el-Kareh, Secomb, "Theoretical models for drug delivery in solid tumors," *Crit. Rev. Biomed. Eng.*, 25(6):503-71, 1997.

Erlandsson, "Molecular genetics of renal cell carcinoma," *Cancer Genet. Cytogenet.*, 104(1):1-18, 1998.

Feigner, P. L. et al. *Proc. Natl. Acad. Sci. USA* 84:7413, 1987.

Feng and Holland, *Nature*, 334:6178, 1988.

Firak and Subramanian, *Mol. Cell. Biol.*, 6:3667, 1986.

Foecking and Hofstetter, "Powerful and versatile enhancer-promoter unit for mammalian expression vectors," *Gene*, 45(1):101-5, 1986.

Fraley et al., "Entrapment of a bacterial plasmid in phospholipid vesicles: Potential for gene transfer," *Proc. Nat'l Acad. Sci. USA*, 76:3348-3352, 1979.

Frixen et al., *J. Cell Biol.*, 113:173-185, 1991.

Fujita et al., *Cell*, 49:357, 1987.

Fujiwara, T. et al. Induction of chemosensitivity in human lung cancer cells in vivo by adenoviral-mediated transfer of the wild-type p53 gene. *Cancer Res.* 54, 2287-2291 (1994).

Fujiwara, T. et al. A retroviral wild-type p53 expression vector penetrates human lung cancer spheroids and inhibits growth by inducing apoptosis. *Cancer Res.* 53, 4129-4133 (1993).

Gabizon et al., "Effect of liposome composition and other factors on the targeting of liposomes to experimental tumors: biodistribution and imaging studies," *Cancer Res.*, 50(19):6371-8, 1990.

Georges, R. N., Mukhopadhyay, T., Zhang, Y., Yen, N. & Roth, J. A. Prevention of orthotopic human lung cancer growth by intratracheal instillation of a retroviral antisense K-ras construct. *Cancer Res.* 53, 1743-1746 (1993).

Gertig and Hunter, "Genes and environment in the etiology of colorectal cancer," *Semin. Cancer Biol.*, 8(4):285-298, 1997.

Ghosh and Bachhawat, "Targeting of liposomes to hepatocytes," *In: Liver diseases, targeted diagnosis and therapy using specific receptors and ligands*," Wu G. and C. Wu ed. New York: Marcel Dekker, pp. 87-104, 1991.

Giancotti and Ruoslahti, *Cell*, 60:849-859, 1990.

Gilles et al., *Cell*, 33:717, 1983.

Gilliland et al., *Proc. Natl. Acad. Sci. USA*, 77:4539-4543, 1980.

Gloss et al., *EMBO J.*, 6:3735, 1987.

Godbout et al., *Mol. Cell. Biol.*, 8:1169, 1988.

Goodbourn and Maniatis, *Proc. Nat'l Acad. Sci. USA*, 85:1447, 1988.

Goodbourn et al., *Cell*, 45:601, 1986.

Greene et al., *Immunology Today*, 10:272, 1989.

Grosschedl and Baltimore, *Cell*, 41:885, 1985.

Hamada, K. et al. Adenovirus-mediated transfer of a wild-type p53 gene and induction of apoptosis in cervical cancer. *Cancer Res.* 56, 3047-3054 (1996). Hanibuchi, Yano, Nishioka, Yanagawa, Kawano, Sone, "Therapeutic efficacy of mouse-human chimeric antiganglioside GM2 monoclonal antibody against multiple organ micrometastases of human lung cancer in NK cell-depleted SCID mice," *Int. J. Cancer*, 78(4):480-5, 1998.

Hara et al., *Biochim Biophys ACTA*, 1278:51-58, 1996.

Hartmann et al., "High frequency of p53 gene mutations in primary breast cancers in Japanese women, a low-incidence population," *Br. J. Cancer*, 73(8):896-901, 1996.

Hartmann et al., "Overexpression and mutations of p53 in metastatic malignant melanomas," *Int. J. Cancer*, 67(3): 313-317, 1996.

Haslinger and Karin, *Proc. Nat'l Acad. Sci. USA.*, 82:8572, 1985.
Hauber and Cullen, *J. Virology*, 62:673, 1988.
Hellstrand, Hermodsson, Naredi, Mellqvist, Brune, "Histamine and cytokine therapy," *Acta. Oncol.*, 37(4):347-53, 1998.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Ho, Lau, Leung, Johnson, "Internal radiation therapy for patients with primary or metastatic hepatic cancer: a review," *Cancer*, 83(9):1894-907, 1998.
Holbrook et al., *Virology*, 157:211, 1987.
Hollstein M, Sidransky D, Vogelstein B, Harris C C, "p53 mutations in cancer," *Science* 253:49-53, 1991.
Horlick and Benfield, *Mol. Cell. Biol.*, 9:2396, 1989.
Huang et al., *Cell*, 27:245, 1981.
Hui and Hashimoto, "Pathways for potentiation of immunogenicity during adjuvant-assisted immunizations with *Plasmodium falciparum* major merozoite surface protein 1," *Infect. Immun.*, 66(11):5329-36, 1998.
Hussussian et al., *Nature Genetics*, 15-21, 1994.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Irie & Morton, "Regression of cutaneous metastatic melanoma by intralesional injection with human monoclonal antibody to ganglioside GD2," *Proc. Nat'l Acad. Sci. USA* 83:8694-8698, 1986
Irie et al., "Melanoma gangliosides and human monoclonal antibody," In: *Human Tumor Antigens and Specific Tumor Therapy*, Metzgar & Mitchell (eds.), Alan R. Liss, Inc., New York, pp. 115-126, 1989.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Ji, L. et al. Induction of apoptosis and inhibition of tumorigenicity and tumor growth by adenovirus vector-mediated FHIT gene overexpression. *Cancer Res.* 59, 3333-3339 (1999).
Johnson et al., *Mol. Cell. Biol.*, 9:3393, 1989.
Johnson, Hamdy, "Apoptosis regulating genes in prostate cancer (review)," *Oncol. Rep.*, 5(3):553-7, 1998.
Ju, D W, Tao Q, Cheng D S, Zhang W, Zhang M, Hamada H, Cao X, "Adenovirus-mediated lymphotactin gene transfer improves therapeutic efficacy of cytosine deaminase suicide gene therapy in established murine colon carcinoma," *Gene Ther.*, 7(4):329-38, 2000.
Kadesch and Berg, *Mol. Cell. Biol.*, 6:2593, 1986.
Kamb et al., *Nature Genetics*, 8:22-26, 1994.
Kamb et al., *Science*, 2674:436-440, 1994.
Kaneda et al., "Increased expression of DNA cointroduced with nuclear protein in adult rat liver," *Science*, 243:375-378, 1989.
Karin et al., *Mol. Cell. Biol.*, 7:606, 1987.
Kataoka, M. et al. An agent that increases tumor suppressor transgene product coupled with systemic transgene delivery inhibits growth of metastatic lung cancer in vivo. *Cancer Res.* 58, 4761-4765 (1998).
Katinka et al., *Cell*, 20:393, 1980.
Katinka et al., *Nature*, 290:720, 1981.
Kato et al., "Expression of hepatitis β virus surface antigen in adult rat liver," *J. Biol. Chem.*, 266:3361-3364, 1991.
Kawamoto et al., *Mol. Cell. Biol.*, 8:267, 1988.
Kerr et al., "Apoptosis: a basic biological phenomenon with wide-ranging implications in tissue kinetics," *Br. J. Cancer*, 26(4):239-57, 1972.
Kiledjian et al., *Mol. Cell. Biol.*, 8:145, 1988.
Klamut et al., *Mol. Cell. Biol.*, 10:193, 1990.
Koch et al., *Mol. Cell. Biol.*, 9:303, 1989.
Kolmel, "Cytology of neoplastic meningosis," *J. Neurooncol.*, 38(2-3):121-125, 1998.
Kriegler and Botchan, In: *Eukaryotic Viral Vectors*, Y. Gluzman, ed., Cold Spring Harbor: Cold Spring Harbor Laboratory, N Y, 1982.
Kriegler and Botchan, *Mol. Cell. Biol.*, 3:325, 1983.
Kriegler et al., *Cell*, 38:483, 1984a.
Kriegler et al., *Cell*, 53:45, 1988.
Kriegler et al., In: *Cancer Cells 2/Oncogenes and Viral Genes*, Van de Woude et al. eds, Cold Spring Harbor, Cold Spring Harbor Laboratory, 1984b.
Kriegler et al., In: Gene Expression, D. Hamer and M. Rosenberg, eds., New York: Alan R. Liss, 1983.
Kuhl et al., *Cell*, 50:1057, 1987.
Kunz et al., *Nucl. Acids Res.*, 17:1121, 1989.
Larsen et al., *Proc. Nat'l Acad. Sci. USA.*, 83:8283, 1986.
Laspia et al., *Cell*, 59:283, 1989.
Latimer et al., *Mol. Cell. Biol.*, 10:760, 1990.
Lee et al., *Mol. Endocrinol.*, 2: 404-411, 1988.
Lee et al., *Nature*, 294:228, 1981.
Levine, A. J., Momand, J., and Finlay, C. A. "The p53 tumor suppresor gene," *Nature*, 351:453-456, 1991.
Levinson et al., *Nature*, 295:79, 1982.
Liebermann, Gregory, Hoffman, "AP-1 (Fos/Jun) transcription factors in hematopoietic differentiation and apoptosis," *Int. J. Oncol.*, 12(3):685-700, 1998.
Lin et al., *Mol. Cell. Biol.*, 10:850, 1990.
Lin and Guidotti, *J. Biol. Chem.*, 264:14408-14414, 1989.
Liu et al. *J. Biol. Chem.* 270:24864, 1995.
Luria et al., *EMBO* 1, 6:3307, 1987.
Lusky and Botchan, *Proc. Nat'l Acad. Sci. USA.*, 83:3609, 1986.
Lusky et al., *Mol. Cell. Biol.*, 3:1108, 1983.
Macejak and Sarnow, "Internal initiation of translation mediated by the 5' leader of a cellular mRNA," *Nature*, 353:90-94, 1991.
Magi-Galluzzi, Murphy, Cangi, Loda, "Proliferation apoptosis and cell cycle regulation in prostatic carcinogenesis," *Anal. Quant. Cytol. Histol.*, 20(5):343-350, 1998.
Majors and Varmus, *Proc. Nat'l Acad. Sci. USA.*, 80:5866, 1983.
Mangray and King, "Molecular pathobiology of pancreatic adenocarcinoma," *Front Biosci.*, 3:D1148-1160, 1998.
Martin, F. J., in Specialized Drug Delivery Systems-Manufacturing and Production Technology, (P. Tyle Ed.) Marcel Dekker, New York, pp. 267-316, 1990.
Matsura et al., *Brit. J. Cancer*, 66:1122-1130, 1992.
Mayer, Future developments in the selectivity of anticancer agents: drug delivery and molecular target strategies," *Cancer Metastasis Rev.*, 17(2):211-8, 1998.
McNeall et al., *Gene*, 76:81, 1989.
Miksicek et al., *Cell*, 46:203, 1986.
Mitchell et al., "Active specific Immunotherapy of melanoma with allogeneic cell lysates: Rationale, results and possible mechanisms of action," *Ann. N.Y. Acad. Sci.*, 690:153-166, 1993.
Mitchell et al., "Active-Specific Immunotherapy for Melanoma," *J. Clin. Oncol.*, 8(5):856-859, 1990.
Mordacq and Linzer, *Genes and Dev.*, 3:760, 1989.
Moreau et al., *Nucl. Acids Res.*, 9:6047, 1981.

Mori et al., *Cancer Res.*, 54:3396-3397, 1994.

Morton D. L., and Ravindranath, M. H. Current concepts concerning melanoma vaccines. In *Tumor Immunology*, Dalgleish A G (ed.), London: Cambridge University Press, 1-55, 1996.

Morton, D. L., Foshag, L. J., Hoon, D. S., Nizze, J. A., Wanek, L. A., Chang, C., Davtyan, D. G., Gupta, R. K., Elashoff, R., and Irie, R. F. Prolongation of survival in metastatic melanoma after active specific immunotherapy with a new polyvalent melanoma vaccine. *Ann. Surg.* 216: 463-482, 1992.

Mougin, Bernard, Lab, "Biology of papillomavirus II infections. Their role in the carcinogenesis of the cervix," *Ann. Biol. Clin.* (Paris), 56(1):21-8, 1998.

Muesing et al., *Cell*, 48:691, 1987.

Mumby and Walter, "Protein phosphatases and DNA tumor viruses: transformation through the back door?" *Cell Regul.*, 2(8):589-598, 1991.

Natoli, Costanzo, Guido, Moretti, Levrero, Ápoptotic, non-apoptotic, and anti-apoptotic pathways of tumor necrosis factor signalling," *Biochem. Pharmacol.*, 56(8):915-920, 1998.

Ng et al., *Nuc. Acids Res.*, 17:601, 1989.

Nicolau et al., *Methods Enzymol.*, 149:157-176, 1987.

Nicolau and Sene, "Liposome-mediated DNA transfer in eukaryotic cells," *Biochem. Biophys. Acta*, 721:185-190, 1982.

Nobri et al., *Nature*, 368:753-756, 1995.

Obrink, *BioEssays*, 13:227-233, 1991.

Ochi, Hasuoka, Mizushima, Matsumura, Harada, "A case of small pancreatic cancer diagnosed by serial follow-up studies promptly by a positive K-ras point mutation in pure pancreatic juice," *Am. J. Gastroenterol.*, 93(8):1366-1368, 1998.

Odin and Obrink, *Exp. Cell Res.*, 171:1-15, 1987.

Ohara, "Radiotherapy: a significant treatment option in management of prostatic cancer," *Gan. To. Kagaku. Ryoho.*, 25(6):823-8, 1998.

Okamoto et al., *Proc. Nat'l Acad. Sci. USA*, 91:11045-11049, 1994.

Ondek et al., *EMBO 1*, 6:1017, 1987.

Orlow et al., *Cancer Res.*, 54:2848-2851, 1994.

Omitz et al., *Mol. Cell. Biol.*, 7:3466, 1987.

Palmiter et al., *Nature*, 300:611, 1982.

Pech et al., *Mol. Cell. Biol.*, 9:396, 1989.

Pelletier and Sonenberg, *Nature*, 334:320-325, 1988.

Perez-Stable and Constantini, *Mol. Cell. Biol.*, 10:1116, 1990.

Philip et al. *J. Biol. Chem.*, 268:16087, 1993.

Picard and Schaffner, *Nature*, 307:83, 1984.

Pietras, Pegram, Finn, Maneval, Slamon, "Remission of human breast cancer xenografts on therapy with humanized monoclonal antibody to HER-2 receptor and DNA-reactive drugs," *Oncogene*, 17(17):2235-49, 1998.

Pinkert et al., *Genes and Dev.*, 1:268, 1987.

Ponta et al., *Proc. Nat'l Acad. Sci. USA.*, 82:1020, 1985.

Porton et al., *Mol. Cell. Biol.*, 10:1076, 1990.

Qin, Tao, Dergay, Moy, Fawell, Davis, Wilson, Barsoum, "Interferon-beta gene therapy inhibits tumor formation and causes regression of established tumors in immune-deficient mice," *Proc. Nat'l Acad. Sci. USA*, 95(24):1411-6, 1998.

Queen and Baltimore, *Cell*, 35:741, 1983.

Quinn et al., *Mol. Cell. Biol.*, 9:4713, 1989.

Ravindranath, M. H. and Morton, D. L. Role of gangliosides in active immunotherapy with melanoma vaccine. *Intern. Rev. Immunol.* 7: 303-329, 1991.

Redondo et al., *Science*, 247:1225, 1990.

Reisman and Rotter, *Mol. Cell. Biol.*, 9:3571, 1989.

Resendez Jr. et al., *Mol. Cell. Biol.*, 8:4579, 1988.

Rittling et al., *Nucl. Acids Res.*, 17:1619, 1989.

Rosen et al., *Cell*, 41:813, 1988.

Rosenberg et al., *Ann. Surg.*, 210:474, 1989.

Rosenberg et al., *N. Engl. J. Med.*, 319:1676, 1988.

Rovere P, Sabbadini M G, Vallinoto C, Fascio U, Zimmermann, VS, Bondanza A, Ricciardi-Castagnoli P, Manfredi A A, "Delayed clearance of apoptotic lymphoma cells allows cross-presentation of intracellular antigens by mature dendritic cells," *J Leukoc Biol.* 66(2):345-9, 1999.

Satake et al., *J. Virology*, 62:970, 1988.

Schaffner et al., *J. Mol. Biol.*, 201:81, 1988.

Searle et al., *Mol. Cell. Biol.*, 5:1480, 1985.

Serrano et al., *Nature*, 366:704-707, 1993.

Serrano et al., *Science*, 267:249-252, 1995.

Sharp and Marciniak, *Cell*, 59:229, 1989.

Shaul and Ben-Levy, *EMBO J.*, 6:1913, 1987.

Sherman et al., *Mol. Cell. Biol.*, 9:50, 1989.

Sleigh and Lockett, *J. EMBO*, 4:3831, 1985.

Soddu and Sacchi, "p53: prospects for cancer gene therapy," *Cytokines Cell Mol. Ther.*, 4(3):177-185, 1998.

Solodin et al. *Biochemistry* 34:13537, 1995.

Solyanik, Berezetskaya, Bulkiewicz, Kulik, "Different growth patterns of a cancer cell population as a function of its starting growth characteristics: analysis by mathematical modelling," *Cell Prolif*, 28(5):263-278, 1995.

Sozzi, G. et al. Absence of Fhit protein in primary lung tumors and cell lines with FHIT gene abnormalities. *Cancer Res.* 57, 5207-5212 (1997).

Spalholz et al., *Cell*, 42:183, 1985.

Spandau and Lee, J. Virology, 62:427, 1988.

Spandidos and Wilkie, *EMBO 1*, 2:1193, 1983.

Spanjer and Scherphof, *Biochim Biophys ACTA*, 734:40-47, 1983.

Steinman R M, Inaba K, Turley S, Pierre P, Mellman I, "Antigen capture, processing, and presentation by dendritic cells: recent cell biological studies," *Hum Immunol.* 60(7):562-7, 1999.

Stephens and Hentschel, *Biochem. 1*, 248:1, 1987.

Stokke, Smedshammer, Jonassen, Blomhoff, Skarstad, Steen, "Uncoupling of the order of the S and M phases: effects of staurosporine on human cell cycle kinases," *Cell Prolif.*, 30(5):197-218, 1997.

Stuart et al., *Nature*, 317:828, 1985.

Sullivan and Peterlin, *Mol. Cell. Biol.*, 7:3315, 1987.

Suzuki et al., *FEBS Letters*, 425:436-440, 1998.

Swartzendruber and Lehman, *J. Cell. Physiology*, 85:179, 1975.

Takebe et al., *Mol. Cell. Biol.*, 8:466, 1988.

Tavernier et al., *Nature*, 301:634, 1983.

Taylor and Kingston, *Mol. Cell. Biol.*, 10:165, 1990a.

Taylor and Kingston, *Mol. Cell. Biol.*, 10:176, 1990b.

Taylor et al., *J. Biol. Chem.*, 264:15160, 1989.

Templeton et al., "Improved DNA: liposome complexes for increased systemic delivery and gene expression," *Nat. Biotechnol.*, 15(7):647-52, 1997.

Thierry, A. R. et al. *Proc. Natl. Acad. Sci. USA* 92:9742, 1995.

Thiesen et al., *J. Virology*, 62:614, 1988.

Treisman, Cell, 42:889, 1985.

Tronche et al., *Mol. Biol. Med.*, 7:173, 1990.

Trudel and Constantini, *Genes and Dev.*, 6:954, 1987.

Tsujimoto, Croce, "Analysis of the structure, transcripts, and protein products of bcl-2, the gene involved in human follicular lymphoma," Proc. Natl. Acad. Sci. USA, 83(14): 5214-8, 1986.
Tsujimoto et al., "Involvement of the bcl-2 gene in human follicular lymphoma," Science, 228(4706):1440-3, 1985.
Tsukamoto, M. et al. Nature Genetics 9:243, 1995.
Tyndall et al., Nuc. Acids. Res., 9:6231, 1981.
Umbas et al., Cancer Res., 52:5104-5109, 1992.
Vannice and Levinson, J. Virology, 62:1305, 1988.
Vasseur et al., Proc. Nat'l Acad. Sci. USA., 77:1068, 1980.
Vogelstein and Kinzler, "p53 function and dysfunction," Cell, 70(4):523-526, 1992.
Wang and Calame, Cell, 47:241, 1986.
Weber et al., Cell, 36:983, 1984.
Weinberg, Science, 254:1138-1145, 1991.
Weinberger et al. Mol. Cell. Biol., 8:988, 1984.
Winoto and Baltimore, Cell, 59:649, 1989.
Wong et al., "Appearance of β-lactamase activity in animal cells upon liposome mediated gene transfer," Gene, 10:87-94, 1980.
Yang, J and Huang, L Gene Therapy 4:950-960, 1997.
Yutzey et al. Mol. Cell. Biol., 9:1397, 1989.
Zhu et al., Science 261:209 1993.

3. The method of claim 1, wherein the composition is administered intravenously to the patient.

4. The method of claim 1, wherein the composition is administered to the patient before chemotherapy, surgery, immunotherapy, hormonal therapy, or radiotherapy.

5. The method of claim 4, wherein the composition is administered less than 72 hours prior to chemotherapy, surgery, immunotherapy, hormonal therapy, or radiotherapy.

6. The method of claim 5, wherein the composition is administered less than 24 hours prior to chemotherapy, surgery, immunotherapy, hormonal therapy, or radiotherapy.

7. The method of claim 1, wherein the composition is administered during chemotherapy, surgery, immunotherapy, hormonal therapy, or radiotherapy.

8. The method of claim 1, wherein the composition is administered after chemotherapy, surgery, immunotherapy, hormonal therapy, or radiotherapy.

9. The method of claim 8, wherein the composition is administered less than 72 hours after chemotherapy, surgery, immunotherapy, hormonal therapy, or radiotherapy.

10. The method of claim 9, wherein the composition is administered less than 24 hours after chemotherapy, surgery, immunotherapy, hormonal therapy, or radiotherapy.

What is claimed is:

1. A method of treating a patient for lung metastatic cancer comprising systemically administering to the patient an effective amount of a pharmaceutically acceptable composition comprising:
   a) an extruded lipid formulation comprising DOTAP in a concentration range from about 1 mM to about 8 mM and at least one cholesterol or cholesterol mixture, and
   b) a nucleic acid under the control of a promoter, wherein the nucleic acid encodes a polypeptide that induces apoptosis in a metastatic lung cancer cell, thereby treating said metastatic lung cancer in said patient.

2. The method of claim 1, wherein the composition is administered more than one time.

11. The method of claim 1, wherein the composition comprises DOTAP in a concentration range from about 2 mM to about 7 mM.

12. The method of claim 11, wherein the composition comprises DOTAP in a concentration range from about 3 mM to about 6 mM.

13. The method of claim 12, wherein the composition comprises DOTAP in a concentration range from about 4 mM to about 5 mM.

14. The method of claim 1, wherein the composition comprises at least one cholesterol or cholesterol mixture in a concentration ranging from about 2 mM to about 7 mM.

15. The method of claim 14, wherein the composition comprises at least one cholesterol or cholesterol mixture in a concentration ranging from about 3 mM to about 6 mM.

16. The method of claim 15, wherein the composition comprises at least one cholesterol or cholesterol mixture in a concentration ranging from about 4 mM to about 5 mM.

17. The method of claim 1, wherein the composition comprises DOTAP and at least one cholesterol or cholesterol mixture in a molar ratio from about 3:1 to about 1:3.

18. The method of claim 17, wherein the composition comprises DOTAP and at least one cholesterol or cholesterol mixture in a molar ratio of about 1:1.

19. The method of claim 1, wherein the polypeptide is Rb, p53, p14, p15, p16, p19, INK4c, p21, p27, p73, a p16-p27 fusion, a p21-p27 fusion, $p56^{RB}$, E2F-1, NOEY2, DCC, APC, NF-1, NF-2, PTEN, FHIT, C-CAM, E-cadherin, MEN-I, MEN-II, ZAC1, VHL, FCC, MCC, PMS1, PMS2, MLH-1, MSH-2, DPC4, BRCA1, BRCA2, mda-7, DBCCR-1 or WT-1.

20. The method of claim 19, wherein the polypeptide is p53.

21. The method of claim 1, wherein the composition further comprises a targeting moiety.

22. The method of claim 21, wherein the targeting moiety is a peptide, a ligand, or an antibody.

23. The method of claim 22, wherein the targeting moiety comprises a peptide that includes an RGD sequence.

24. The method of claim 23, wherein the peptide includes an RGDFV sequence.

25. The method of claim 24, wherein the peptide is from 3 to 30 amino acids in length.

26. The method of claim 25, wherein the peptide is from 3 to 20 amino acids in length.

27. The method of claim 26, wherein the peptide is from 4 to 10 amino acids in length.

28. The method of claim 24, wherein the peptide is a cyclic peptide.

29. The method of claim 28, wherein the cyclic peptide is 5 amino acids in length.

30. The method of claim 21, wherein the targeting moiety comprises a ligand for a cell surface protein.

31. The method of claim 30, wherein the cell surface protein is an integrin, proteoglycan, glycoprotein, receptor, or transporter.

32. The method of claim 21, wherein the targeting moiety comprises an antibody that binds to a cell surface protein.

33. The method of claim 32, wherein the antibody is an antibody to the Her-1 receptor.

34. The method of claim 1, wherein the promoter is CMV IE, CEA, VEGF, AFP, lung surfactant promoter, dectin-1, dectin-2, human CD11c, F4/80, SM22, CEA, tyrosinase, tet-inducible or tet-repressible, Rous Sarcoma Virus, MLP, or MHC class II promoter.

35. The method of claim 19, wherein the polypeptide is FHIT.

36. The method of claim 19, wherein the polypeptide is mda7.

37. The method of claim 1, wherein the cholesterol is cholesterol acetate or cholesterol oleate.

38. The method of claim 1, wherein the survival of the patient is increased.

* * * * *

UNITED STATES PATENT AND TRADEMARK OFFICE
CERTIFICATE OF CORRECTION

PATENT NO. : 10,293,056 B1
APPLICATION NO. : 09/575473
DATED : May 21, 2019
INVENTOR(S) : Rajagopal Ramesh et al.

Page 1 of 1

It is certified that error appears in the above-identified patent and that said Letters Patent is hereby corrected as shown below:

On the Title Page

Related U.S. Application Data, item (60), insert --Provisional application No. 60/135,818, filed on May 24, 1999.--.

Signed and Sealed this
Twenty-sixth Day of November, 2019

Andrei Iancu
*Director of the United States Patent and Trademark Office*